US009982240B2

(12) United States Patent
Legastelois et al.

(10) Patent No.: US 9,982,240 B2
(45) Date of Patent: May 29, 2018

(54) PRODUCTION OF INFECTIOUS INFLUENZA VIRUSES

(71) Applicant: SANOFI PASTEUR, Lyons (FR)

(72) Inventors: Isabelle Legastelois, Saint Andeol le Chateau (FR); Julie Medina, Lentilly (FR); Catherine Moste, Charbonnieres les Bains (FR)

(73) Assignee: Sanofi Pasteur, Lyons (FR)

( * ) Notice: Subject to any disclaimer, the term of this patent is extended or adjusted under 35 U.S.C. 154(b) by 70 days.

(21) Appl. No.: 14/419,235

(22) PCT Filed: Jul. 29, 2013

(86) PCT No.: PCT/EP2013/065920
§ 371 (c)(1),
(2) Date: Feb. 2, 2015

(87) PCT Pub. No.: WO2014/019990
PCT Pub. Date: Feb. 6, 2014

(65) Prior Publication Data
US 2015/0191703 A1 Jul. 9, 2015

(30) Foreign Application Priority Data
Aug. 3, 2012 (EP) ..................................... 12305968

(51) Int. Cl.
C12N 7/00 (2006.01)
C12N 15/85 (2006.01)
A61K 39/145 (2006.01)
A61K 39/00 (2006.01)

(52) U.S. Cl.
CPC .............. C12N 7/00 (2013.01); A61K 39/145 (2013.01); C12N 15/85 (2013.01); A61K 2039/5254 (2013.01); C12N 2760/00051 (2013.01); C12N 2760/00052 (2013.01); C12N 2760/16134 (2013.01); C12N 2760/16151 (2013.01); C12N 2760/16164 (2013.01); C12N 2760/16234 (2013.01); C12N 2760/16251 (2013.01); C12N 2760/16264 (2013.01)

(58) Field of Classification Search
None
See application file for complete search history.

(56) References Cited

U.S. PATENT DOCUMENTS

| | | | |
|---|---|---|---|
| 5,994,128 A | 11/1999 | Fallaux et al. | |
| 2004/0142003 A1 | 7/2004 | Palese et al. | |
| 2007/0059834 A1 | 3/2007 | Mueller-Hartmann et al. | |
| 2008/0254065 A1* | 10/2008 | Podda | A61K 39/145 424/206.1 |
| 2009/0246830 A1 | 10/2009 | Kawaoka et al. | |
| 2011/0143424 A1 | 6/2011 | Kawaoka et al. | |
| 2011/0159543 A1 | 6/2011 | Verschuur et al. | |
| 2012/0058538 A1 | 3/2012 | Palese et al. | |

FOREIGN PATENT DOCUMENTS

| | | |
|---|---|---|
| CN | 1970081 A | 5/2007 |
| WO | 2001083794 A2 | 11/2001 |
| WO | 2005062820 A9 | 10/2005 |
| WO | 2009152181 A1 | 12/2009 |

OTHER PUBLICATIONS

Sanofi-Pasteur 2009-2010 seasonal influenza Fluzone® package insert, 2009.*
Baron and Barrett, "Rescue of rinderpest virus from cloned cDNA," 1997, J Virol, 71(2):1265-1271.
Bridgen and Elliott, "Rescue of a segmented negative-strand RNA virus entirely from cloned complementary DNAs," 1996, Proc Natl Acad Sci USA, 93(26):15400-15404.
Coussens et al, "Immortalized chick embryo cell line adapted to serum-free growth conditions and capable of replicating human and reassortant H5N1 influenza strains for vaccine production," 2011, Vaccine, 29(47):8661-8668.
De Ona et al, "Isolation of influenza virus in human lung embryonated fibroblast cells (MRC-5) from clinical samples," 1995, J Clin Microbiol, 33(7):1948-1949.
De Wit E et al, "A reverse-genetics system for Influenza A virus using T7 RNA polymerase," 2007, Journal of General Virology, 88(4): 1281-1287.
Durbin et al, "Recovery of infectious human parainfluenza virus type 3 from cDNA," 1997, Virology, 235(2):323-332.
FluGen Inc.,: "FluGen's CHO-cell-based production system generates egg-free, 2009 H1N1 influenza vaccine virus," Oct. 30, 2009, http://www.news-medical.net/news/20091030/FluGens-CHO-cell-based-production-systems-generates-egg-free-2009-H1N1-influenza-vaccine-virus.aspx.
Fodor E et al.: "Rescue of influenza A virus from recombinant DNA", 1999, Journal of Virology, 73(11):9679-9682.
Garcin et al, "A highly recombinogenic system for the recovery of infectious Sendai paramyxovirus from cDNA: generation of a novel copy-back nondefective interfering virus," 1995, EMBO J, 14(24):6087-6094.
Gerdil et al, "The annual production cycle for influenza vaccine," 2003, Vaccine, 21(16):1776-1779.
Harcum SW, "Effects of Cell Culture Conditions on Terminal Glycosylation Efficiency in Chinese Hamster Ovary (CHO) Cells", Dec. 31, 2010, http://portal.nifa.usda.gov/web/crisprojectpages/0206588-effects-of-cell-culture-conditions-on-terminal-glycosylation-efficiency-in-chinese-hamster-ovary-cho-cells.html, p. 1-3.
He et al, "Recovery of infectious SV5 from cloned DNA and expression of a foreign gene," 1997, Virology, 237 (2):249-260.

(Continued)

Primary Examiner — Benjamin P Blumel
(74) Attorney, Agent, or Firm — McNeill Baur PLLC

(57) ABSTRACT

The invention relates to a method for producing influenza infectious viruses wherein CHO cells are infected with a seed of infectious influenza virus which has been generated by transfecting cells with an appropriate set of expression vectors. The invention also relates to a recombination cassette, and to a vector comprising said recombination cassette, that may be used in methods for producing infectious viruses, and particularly in the method according to the invention.

15 Claims, 2 Drawing Sheets

(56) References Cited

OTHER PUBLICATIONS

Figure 1:
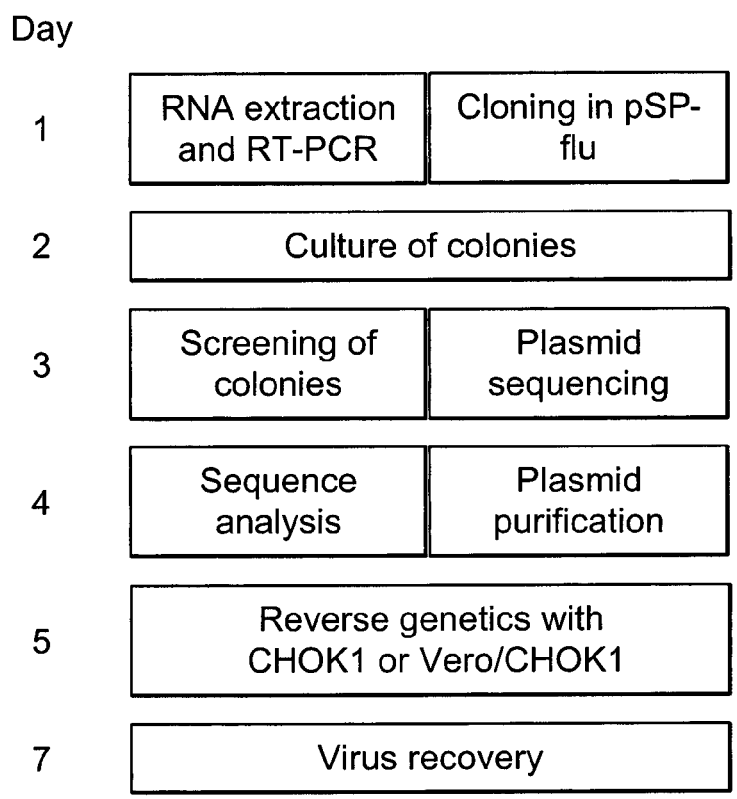

Herfst et al, "Recovery of human metapneumovirus genetic lineages a and B from cloned cDNA," 2004, J Virol, 78 (15):8264-8270.

Hoffman and Banerjee, "An infectious clone of human parainfluenza virus type 3," 1997, J Virol, 71 (6):4272-4277.

Hoffman et al, "A DNA transfection system for generation of influenza A virus from eight plasmids," 2000, PNAS, 97 (11):6108-6113.

Hoffman et al, "Eight-plasmid system for rapid generation of influenza virus vaccines," 2002, Vaccine, 20 (25-26):3165-3170.

International Preliminary Report on Patentability for application PCT/EP2013/065920, dated Feb. 3, 2015.

International Search Report for application PCT/EP2013/065920, dated Aug. 22, 2013.

Iwatsuki-Horimoto et al, "Limited compatibility between the RNA polymerase components of influenza virus type A and B," 2008, Virus Res, 135(1):161-165.

Jackson et al, "Molecular studies of influenza B virus in the reverse genetics era," 2011, J Gen Virol, 92(Pt1):1-17.

Jin et al, "Recombinant human respiratory syncytial virus (RSV) from cDNA and construction of subgroup A and B chimeric RSV," 1998, Virology, 251(1):206-014.

Kawano et al, "Recovery of infectious human parainfluenza type 2 virus from cDNA clones and properties of the defective virus without V-specific cysteine-rich domain," 2001, Virology, 284(1):99-112.

Kistner et al, "Development of a mammalian cell (Vero) derived candidate influenza virus vaccine," 1998, Vaccine, 16(9-10):960-968.

Koudstaal et al, "Suitability of PER.C6 cells to generate epidemic and pandemic influenza vaccine strains by reverse genetics," 2009, Vaccine, 27(19):2588-2593.

Legastelois I et al, "Preparation of genetically engineered A/H5N1 and A/H7N1 pandemic vaccine viruses by reverse genetics in a mixture of Vero and chicken embryo cells," 2007, Influenza and Other Respiratory Viruses, 1 (3):95-98.
Massin et al, "Cloning of the chicken RNA polymerase I promoter and use for reverse genetics of influenza A viruses in avian cells," 2005, J Virol, 79(21):13811-13816.
Murakami et al, "Establishment of canine RNA polymerase I-driven reverse genetics for influenza A virus: its application for H5N1 vaccine production," 2008, J Virol, 82(3):1605-1609.
Neumann et al, "An improved reverse genetics system for influenza A virus generation and its implications for vaccine production," 2005, Proc Natl Acad Sci USA, 102(46)16825-16829.
Neumann et al, "Cloning of the chicken RNA polymerase I promoter and use for reverse genetics of influenza A viruses in avian cells," 1999, Proc Natl Acad Sci USA, 96(16):9345-9350.
Neumann et al, "Reverse genetics demonstrates that proteolytic processing of the Ebola virus glycoprotein is not essential for replication in cell culture," 2002, J Virol, 76(1):406-410.
Nicolson et al, "Generation of influenza vaccine viruses on Vero cells by reverse genetics: an H5N1 candidate vaccine strain produced under a quality system," 2005, Vaccine, 23(22):2943-2952.
Ozawa et al, "An adenovirus vector-mediated reverse genetics system for influenza A virus generation," 2007, J Virol, 81(17):9556-9559.
Pattnaik et al, "Infectious defective interfering particles of VSV from transcripts of a cDNA clone," 1992, Cell, 69 (6):1011-1020.
Pau et al, "The human cell line PER.C6 provides a new manufacturing system for the production of influenza vaccines," 2001, Vaccine, 19(17-19)2716-2721.
Peeters et al, "Rescue of Newcastle disease virus from cloned cDNA: evidence that cleavability of the fusion protein is a major determinant for virulence," 1999, J Virol, 73(6):5001-5009.
Radecke et al, "Rescue of measles viruses from cloned DNA," 1995, EMBO J, 14(23):5773-5784.
Rossman et al, "Influenza virus assembly and budding," 2011, Virology, 411 (2):229-236.
Schickli et al, "Plasmid-only rescue of influenza A virus vaccine candidates," 2001, Philos Trans R Soc Lond Biol Sci, 356(1416):1965-1973.
Schnell et al, "Infectious rabies viruses from cloned cDNA," 1994, EMBO J, 13(18):4195-4203.
Sridharan et al, "Species specificity of the NS1 protein of influenza B virus: NS1 binds only human and non-human primate ubiquitin-like ISG15 proteins," 2010, J Biol Chem, 285(11):7852-7856.
Stech et al, "Rapid and reliable universal cloning of influenza A virus genes by target-primed plasmid amplification," 2008, Nucleic Acid Res, 36(21):e139.
Wang et al, "Simplified recombinational approach for influenza A virus reverse genetics," 2008, J Virol Methods, 151 (1):74-78.
Watson RJ. et al, "A model for intergration of DNA into genome during transformation of Fusarium graminearum," 2008, Fungal Genetics and Biology, 45(10):1348-1363.
Whiteley et al, "Generation of candidate human influenza vaccine strains in cell culture—rehearsing the European response to an H7N1 pandemic threat," 2007, Influenza Other Respir Viruses, 1(4):157-166.
Zhang et al, "A one-plasmid system to generate influenza virus in cultured chicken cells for potential use in influenza vaccine," 2009, J Virol, 83(18):9296-9303.
Yang Jicheng ed. "Cell Engineering," *Chemical Industry Press,* ISBN 7-122-01295-6 (2008) (4 pages including p. 238).
Office Action dated Oct. 24, 2017 for Chinese Patent Application No. 201380051942.6 issued by the issued from the State Intellectual Property Office of People's Republic of China (English Translation) (6 pages).

* cited by examiner

PRODUCTION OF INFECTIOUS INFLUENZA VIRUSES

CROSS REFERENCE TO RELATED APPLICATIONS

This application is a 371 National Stage entry of pending International Application No. PCT/EP2013/065920, filed Jul. 29, 2013, which claims the benefit of EP 12305968.5, filed Aug. 3, 2012, all of which are incorporated by reference in their entirety.

INCORPORATION BY REFERENCE OF MATERIAL IN ASCII TEXT FILE

This application incorporates by reference the Sequence Listing contained in the following ASCII text file being submitted concurrently herewith: File created on Aug. 26, 2016, file name: 2016-08-26 01121-0003-00US ST25.txt, file size: 27,373 bytes.

FIELD OF THE INVENTION

The invention relates to a method for producing influenza infectious viruses wherein CHO cells are infected with a seed of infectious influenza virus which has been generated by transfecting cells with an appropriate set of expression vectors. The invention also relates to a recombination cassette, and to a vector comprising said recombination cassette, that may be used in methods for producing infectious viruses, and particularly in the methods according to the invention.

BACKGROUND OF THE INVENTION

Influenza virus is the causative agent of a highly contagious respiratory illness, commonly named "flu", which affects animals and humans causing public health and economic problems. The influenza virus is an enveloped RNA virus with a segmented genome consisting of single-stranded negative RNA segments. Influenza viruses encompass the three types: influenza A, influenza B and influenza C viruses. Influenza A and B viruses are responsible for human influenza epidemics resulting in the death of over 50 000 people per year (Rossman et al, 2011, Virology, 411(2): 229-236). While influenza A viruses infect both humans and a broad variety of animals (birds, pigs, horses, dogs, cats, etc.), the largest natural reservoir being wild aquatic birds, influenza B viruses are predominantly restricted to humans which is partially caused by the inability of B/NS1 protein to counteract the innate immune response of others species (Sridharan et al, 2010, J Biol Chem, 285(11):7852-7856) and influenza C viruses are isolated from humans and pigs.

The type A viruses have a spherical or filamentous shape and have a size of about 80 to 150 nm. The viral envelope, consisting of a lipid bilayer, is derived from the plasma membrane of the host cell. Spicules formed of surface glycoproteins, HA (hemagglutinin) and NA (neuraminidase), the main targets for the host antibodies, are inserted into this envelope. The M2 protein, which is also embedded in the membrane, is an ion channel that functions mainly during decapsidation of the virus. The matrix protein M1 is located on the inner periphery of the virus associated with the lipid bilayer and with the ribonucleoprotein (RNP). It has a fundamental role in the nucleo-cytoplasmic export of RNPs. In the capsid, the vRNA segments possess noncoding 5' and 3' ends containing the signals necessary for the transcription, the replication and the encapsidation of the viral genome. The eight vRNA of influenza A viruses called PA (Polymerase Acidic), PB1 (Polymerase Basic protein 1), PB2 (Polymerase Basic protein 2), NP (Nucleoprotein), HA, NA, M and NS (Non-Structural protein) encode one or more proteins by alternative splicing. The PA segment encodes the PA protein; the PB1 segment encodes the PB1, PB1-F2 and PB1-N40 proteins; the NP segment encodes the NP protein; the HA segment encodes the HA protein; the NA segment encodes the NA protein; the M segment encodes the M1 and M2 proteins; the NS segment encodes the nonstructural proteins NS1 and NS2 or NEP (Nuclear Export of vRNPs). The vRNAs are coiled over NP which binds 24 nucleotides per monomer, the polymerase complex binds to the two ends of the RNA molecule, forming an hairpin structure. This complex consists of PB1, PB2 and PA. The RNA, NP and polymerase combination forms the ribonucleoprotein (RNP) complex.

Type B viruses have a glycoprotein in addition to NA called NB which has a type III structure like the protein M2.

Type C viruses have only one multifunctional surface glycoprotein, "hemagglutinin-esterase-fusion protein" (HEF).

Thus, the genome of types A and B viruses contains 8 viral RNA (vRNA) while the genome of the influenza virus type C contains only 7.

Influenza A viruses are also divided into distinct subtypes according to the nature of the surface viral glycoproteins, i.e. currently hemagglutinin (HA) (H1 to H17) and neuraminidase (NA) (N1 to N9).

The discovery by Burnet, in 1936, that influenza virus could grow in embryonated hen's eggs has enabled the study of their properties and has permitted the development of inactivated vaccines (De Ona et al, 1995, J Clin Microbiol, 33(7):1948-1949). As described by the World Heath Organization (WHO), vaccination is the most effective way to prevent infection. Fortunately, safe and effective vaccines have been available for more than 70 years. The seasonal flu vaccine contains different influenza types and subtypes (A/H1N1, A/H3N2 and B) that are updated twice a year (once for the northern hemisphere and once for the southern) because of antigenic modifications. For this reason, the WHO coordinates a Global Influenza Surveillance Network (GISN) to monitor the epidemiology of influenza viruses. Once the viruses to be included in next seasonal vaccine have been determined, candidate high-growth seed virus strains must be prepared by WHO Collaborating Centers like the New York Medical College (NYMC, US), the National Institute for Biological Standards and Control (NIBSC, UK), the CSL group (Australia) and the National Institute for Infectious Diseases (NIID, Japon) (Gerdil et al, 2003, Vaccine, 21(16):1776-1779). Vaccine strains are then amplified on eggs, MDCK or Vero cell lines by manufacturers (Koudstaal et al, 2009, Vaccine, 27(19):2588-2593). Currently, MDCK (Tree et al, 2001, Vaccine, 19(25-26): 3444-3450), Vero (Kistner et al, 1998, Vaccine, 16(9-10): 960-968) and PER.C6® (Pau et al, 2001, Vaccine, 19(17-19):2716-2721) are the three cell lines which may meet the regulatory requirements and have been shown to successfully ensure the replication of influenza A and B viruses. All three cell lines have been adapted to grow in serum free media (Coussens et al, 2011, Vaccine, 29(47):8661-8668).

The introduction of the influenza viruses into the cells (first step of infection) occurs through specific interaction between Influenza hemagglutinin (HA) surface protein and specific cell surface receptors. The host cell membrane receptors specific for influenza viruses are made of carbohydrate structures of sialyl lactosamine chains (sialic acid [Sia] alpha2-3/6 galactose [Gal] beta1-4/3 N-acetyglucosamine) (Suzuki et al, 2011, Adv Exp Med Biol, 705:443-452). Human influenza viruses preferentially bind to cellular receptors containing a Sia2-6Gal linkage, whereas avian viruses preferentially bind to Sia2-3Gal receptors (Coussens et al, 2011, Vaccine, 29(47):8661-8668). When two viruses infect the same cell, different combinations of genomic vRNAs, called reassortants, may arise. This property has been used for the production of influenza A vaccines to combine the antigenic properties of HA and neuraminidase (NA) proteins of target circulating viruses with the favourable growth characteristics (internal genes) of an egg-adapted virus, called A/Puerto Rico/8/34 (PR8) (H1N1). Unfortunately, success in deriving the desired high yielding virus is unpredictable. In addition, some strains cannot be used if they have been isolated on non-validated cell lines as they are not acceptable by the regulatory authorities as a progenitor vaccine strain (Nicolson et al, 2005, Vaccine, 23(22):2943-2952). With respect to influenza type B viruses until very recently no B virus having the growth characteristics of A/PR/8/34 (H1N1) virus has been identified. Therefore, the epidemic circulating (or seasonal) B virus was used directly to infect embryonated hen's eggs and several passages were needed to improve the yield of B vaccine strains (Iwatsuki-Horimoto et al, 2008, Virus Res, 135(1):161-165).

Since 1999, significant improvements in terms of speed and safety were achieved thanks to plasmid-based reverse genetics technology which allows the generation of infectious influenza viruses entirely from cloned viral cDNA (Fodor et al, 1999, J Virol, 73(11):9679-9682). Different systems were developed based on a set of plasmids capable of inducing the expression of the eight vRNAs and at least the polymerase protein complex and the nucleoprotein (NP) required for the transcription. The polymerase protein complex and NP can also be expressed either by transfection of four additional plasmids or by the use of plasmids with bidirectional promoters that allow both vRNA and mRNA synthesis through RNA polymerase I (POL 1) and II (POL 2) (Jackson et al, 2011, J Gen Virol, 92(Pt1):1-17) respectively. The total number of plasmids transfected can vary from 16 (Neuman et al, 1999, Proc Natl Acad Sci USA, 96(16):9345-9350), or 12 (Fodor et al, 1999, J Virol, 73(11): 9679-9682) to 8 (Hoffmann et al, 2002, Vaccine, 20(25-26): 3165-3170), depending if the strategy is unidirectional or bidirectional, and from 3 (Neumann et al, 2005, Proc Natl Acad Sci USA, 102(46):16825-16829) to 1 (Zhang et al, 2009, J Virol, 83(18):9296-9303) if plasmid(s) encode(s) several vRNA.

Current reverse genetics systems are based on the use of PER.C6® (Koudstaal et al, 2009, Vaccine, 27(19):2588-2593), CEP (Chicken Embryo Primary) cells or Chicken Embryonic Fibroblasts (CEF) (Zhang et al, 2009, J Virol, 83(18):9296-9303), 293T cells alone (Neuman et al, 1999, Proc Natl Acad Sci USA, 96(16):9345-9350) or with further amplification on MDCK (Hoffmann et al, 2002, Vaccine, 20(25-26):3165-3170; Schickli et al, 2001, Philos Trans R Soc Lond Biol Sci, 356(1416):1965-1973), Vero cells alone (Nicolson et al, 2005, Vaccine, 23(22):2943-2952; Neumann et al, 2005, Proc Natl Acad Sci USA, 102(46):16825-16829) or with further amplification on Madin-Darby Bovine Kidney (MDBK) (Fodor et al, 1999, J Virol, 73(11):9679-9682), CEP cells or CEF (Legastelois et al, 2007, Influenza Other Respi Viruses, 1(3):95-104; Whiteley et al, 2007, Influenza Other Respi Viruses, 1(4):157-166).

When a mixture of cell lines is used to produce virus by reverse genetics method, the cell line which can be transfected the most efficiently is considered as the one which is responsible for the generation of infectious influenza viruses, while the other cell lines contribute to the multiplication of the infectious viruses. Since human RNA POL I promoter is generally used in the plasmids that allow the production of influenza vRNAs, human and simian cells are the most appropriate cell lines to be used as transfected cell line in the reverse genetics system. However POL I promoter from canine or chicken origin can also be used in canine or avian cells respectively (Massin et al, 2005, J Virol, 79(21): 13811-13816; Murakami et al, 2008, 82(3):1605-1609). On the other hand, the plasmids that allow the production of mRNA encoding viral proteins usually contain a Cytomegalovirus (CMV) or beta actin POLII promoter that can work in any eukaryotic cell (Neuman et al, 1999, Proc Natl Acad Sci USA, 96(16):9345-9350; Schickli et al, 2001, Philos Trans R Soc Lond Biol Sci, 356(1416):1965-1973).

Most of the time, in the above described reverse genetics systems, the cells are usually cultivated in a serum-containing medium to ensure vigorous growth of the different cell types just before transfection. Furthermore, trypsin from porcine origin is also used in the infection medium to sustain viral proliferation after infection. To obtain enough viruses, several amplifications on eggs or cells may also be needed after the first transfection step.

The pandemic A/H1N1 (2009) virus demonstrated the speed with which an influenza A virus can disseminate among the population and illustrated the need for accelerating reassortant production via reverse genetics. Thus, the main challenge is to ensure that high amounts of doses of vaccine are produced in a minimum of time to be distributed all over the world, ideally faster than virus spread.

Conventional approaches used for cloning require restriction enzymes. However restriction sites are often present in different influenza cDNA complementary to vRNA, requiring either the implementation of vector modifications or viral genome mutagenesis. Simplified recombinational approach was developed previously for cloning influenza cDNA complementary to vRNA for reverse genetics purpose (Stech et al, 2008, Nucleic Acid Res, 36(21):e139; Wang et al, 2008, J Virol Methods, 151(1):74-78). Homologous recombination involves a process of breakage and reunion in regions of identical DNA sequences between two DNA molecules to result in new combinations of genetic materiel (Watt et al, 1985, Proc Natl Acad Sci, 82:4768-4772). These previously described recombinational cloning systems are based on a 25 nucleotides recombination cassette comprising the consensus 5' (Uni13) and 3' (Uni12) conserved non-coding ends of influenza A segments between human POL I promoter and terminator. They allow the rapid and direct cloning of any influenza A genome. However, since the nucleotide sequences of vRNA 5' and 3' non-coding ends of influenza B genomes are different from influenza A virus, influenza B genomes cannot be cloned based on this recombination cassette.

Thus there is also a need to develop a universal approach for cloning RNA virus genomes, and in particular the influenza A, B and C genomes, as quickly and as efficiently as possible.

It is an objective of the present invention to provide useful tools and methods that facilitate and/or accelerate the production of an influenza vaccine in optimized safe conditions, especially when a new circulating influenza virus has been identified and could be responsible for an epidemic or a pandemic flu.

To this effect the subject matter of the invention is relating to new methods for producing a large panel of infectious type A and type B viruses, including reassortant or chimeric viruses, in particular viruses that have been generated by reverse genetics. These methods make easier the manufacturing of influenza virus in more secure conditions. In another aspect, the invention provides a universal recombinant vector that allows the cloning of any type of influenza RNA fragment from type A or B viruses, which proved to be a useful tool to carry out reverse genetic methods.

DEFINITIONS

A "promoter" or "promoter sequence" is a DNA regulatory region capable of binding to an RNA polymerase present in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence is found a transcription initiation site (conveniently defined for example, by mapping with nuclease S1), as well as protein binding domains (consensus sequences) responsible for the binding to RNA polymerase. The promoter may be operatively associated with other expression control sequences, including enhancer and repressor sequences. For instance the human RNA Polymerase I promoter (human RNA POLI promoter), is a promoter that binds to human RNA polymerase I; the avian RNA polymerase I promoter is a promoter that binds to avian RNA polymerase I or the T7 polymerase promoter is a promoter that binds to the RNA polymerase of bacteriophage T7.

The terms "vector", "cloning vector" and "expression vector" mean the vehicle by which a DNA (e.g. a foreign gene) can be introduced into a host cell, so as to transform the host and promote expression (e.g. transcription and translation) of the introduced sequence. Vectors include plasmids, phages, recombinant viruses, phagemids, transposons, and artificial chromosomes, etc.; they are discussed in greater detail below.

Vectors typically comprise the DNA of a microorganism, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily be introduced into a suitable host cell. A plasmid vector often contains coding DNA and promoter DNA and has one or more restriction sites suitable for inserting foreign DNA and usually a terminating sequence. Coding DNA is a DNA sequence that encodes a particular amino acid sequence of a particular protein or enzyme or a vRNA segment of a virus. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), pVAX1 plasmids (Life technology, Cergy Pontoise, FR) and many appropriate host cells, using methods disclosed or cited herein or otherwise known to those skilled in the relevant art. Recombinant cloning vectors often include one or more replication systems, one or more markers for selection in the host, e.g. antibiotic resistance, and one or more expression cassettes. Recombinant cloning vector may also contain an antibiotic-free selection system, such as the system described in Peubez et al, 2010, Microbial Cell Factories, 9:65.

As used herein, the term "primer" refers to the function of the oligonucleotide. A primer is an oligonucleotide used for amplifying a target sequence typically by extension of the oligonucleotide after hybridization to the target sequence.

By "RNA polvmerase II" is meant the enzyme that catalyzes, in eukaryotes, the transcription of DNA into mRNA or precursor of mRNA.

By "RNA polvmerase I" is meant the enzyme that catalyzes, in eukaryotes, the transcription of DNA into ribosomal RNA (rRNA) or precursor of rRNA.

The term "unidirectional plasmid" denotes a DNA plasmid containing only one transcription cassette, which allows the transcription of said DNA into rRNA if the transcription cassette contains a polymerase promoter that binds to RNA polymerase I or allows the transcription of said DNA into mRNA if the transcription cassette contains a polymerase promoter that binds to RNA polymerase II. For instance, such plasmids include those described by Neuman et al, 1999, Proc Natl Acad Sci USA, 96(16):9345-9350, and in US 2009/0246830 or US 2011/0143424.

The term "bidirectional plasmid" denotes a DNA plasmid containing two transcription cassettes, which allow the transcription of said DNA into rRNA and into mRNA since the first transcription cassette contains a polymerase promoter that binds to RNA polymerase I and the second transcription cassette contains a polymerase promoter that binds to RNA polymerase II. For instance, such plasmids include those as described by Hoffman et al, 2000, PNAS, 97(11):6108-6113 and in WO 01/83794.

The term "influenza virus" denotes the type species of the Orthomyxoviridae family. Influenza viruses according to the invention are as described hereabove.

Preferably the influenza virus according to the invention is an influenza A or B virus. The influenza A or B virus may be any strain of virus. In particular, the influenza A virus is selected from the group consisting of the H1N1, H2N2, H3N1, H3N2, H3N8, H5N1, H7N1, H7N7, H1N2, H9N2, H7N2, H7N3, and H1ON7 viruses.

By "seasonal or pandemic virus" is meant a clinical isolate of influenza virus that has been isolated from an infected host, such as human.

By "infectious influenza virus" is meant an influenza virus which is able to replicate into a permissive cell. Methods for determining if a virus is infectious are well known by the one skilled in the art. For example, determining if a virus is infectious may be performed using the $TCID_{50}$ assay. The $TCID_{50}$ is a method to assess the amount of infectious virus in a sample (for instance an infected cell culture supernatant, or an infected allantdïc fluid) by introducing incremental dilutions of the sample on permissive cells (such as MDCK cells) and determining the endpoint dilution that induces the infection of 50% of the permissive cells using the Spearman-Karber statistical method.

In some embodiments, said infectious influenza virus may be a reassortant influenza virus, a chimeric influenza virus, or attenuated influenza virus. Preferably, said infectious influenza virus is a reassortant influenza virus. Still preferably, said infectious influenza virus is a reassortant chimeric influenza virus.

By "permissive cells" is meant cells that allow influenza virus to both penetrate into said cells and to achieve its full replication cycle until the production of new infectious virus. Highly permissive cells are cells where influenza viruses actively replicate and produce high amounts of infectious virus.

The term "reassortant virus" denotes a virus which contains genetic material that results from the combination of genetic material of at least two donor viruses. When the reassortant virus is used for preparing a flu vaccine, its genetic material usually contains at least the HA and NA genes from a seasonal or pandemic virus whereas the other genes (backbone genes) are from one or several other donor viruses which have been selected for their ability to grow easily on the substrate of production used for manufacturing the flu vaccine (such as the allantoïc cavity of embryonated hen's eggs or a permissive cell line) and/or to be less or non pathogen for the humans. Examples of donor viruses that contribute as "provider" of backbone genes include A/Puerto Rico/8/34 (H1N1) (A/PR/8/34), B/Lee/40 and/or B/Panama/45/90 viruses.

The term "chimeric virus" denotes a virus which contains chimeric gene encoding chimeric protein. By "chimeric gene and/or protein" is meant that said gene or protein is obtained by the combination of at least two portions of genes or two portions of proteins, as appropriate, derived from at least two different donor viruses. For example, in the case of influenza virus type A or B, said chimeric gene and/or protein may be a chimeric HA and/or chimeric NA vRNA or protein.

The term "attenuated virus" denotes a virus which replicates in a permissive cell but has partially or even totally lost the ability to replicate in animals or humans. Therefore the virulence of an attenuated virus is strongly reduced or even totally absent in humans and animals. The clinical symptoms associated with the infection by an attenuated virus are reduced or even totally absent in animals or humans. Examples of attenuated viruses are well known in the art. An attenuated virus may be prepared, for example, from a wild-type virus by serial passages (for instance on different culture substrates, or at lower temperature than its optimal replication one), recombinant DNA technology, site-directed mutagenesis, genetic manipulation. An attenuated virus useful in the present invention may generate no side effects or side effects of low intensity in the majority of vaccinated individuals, while retaining its ability to induce a protective Immune response in a subject.

The term "inactivated virus" denotes a virus incapable of replication to any significant degree into permissive cells. Viruses may be inactivated by a number of means well known to those skilled in the art. Examples of methods for inactivating a virus include genetic manipulation, chemical or physical treatments, or radiation treatments (including formaldehyde, betapropiolactone, detergents, heat or electromagnetic radiation typically in the forms of X-ray or ultraviolet radiation). In the frame of the invention, useful inactivated influenza viruses are those which have retained the ability to induce a protective immune response in a subject.

The term "reverse genetics" denotes molecular methods to produce infectious, reassortant viruses, or attenuated viruses from their complementary DNAs (cDNAs). These methods are very advantageous for producing reassortant influenza viruses by reassortment of vRNAs between different influenza viruses. The reverse genetics methods are well-known by the one skilled in the art. The reverse genetics methods may be those described hereabove, e.g. the methods using the plasmids described in Neuman et al, 1999, Proc Natl Acad Sci USA, 96(16):9345-9350; Neumann et al, 2005, Proc Natl Acad Sci USA, 102(46):16825-16829; Zhang et al, 2009, J Virol, 83(18):9296-9303; Massin et al, 2005, J Virol, 79(21):13811-13816; Murakami et al, 2008, 82(3):1605-1609; and/or the cells described in Neuman et al, 1999, Proc Natl Acad Sci USA, 96(16):9345-9350; Neumann et al, 2005, Proc Natl Acad Sci USA, 102(46):16825-16829; Zhang et al, 2009, J Virol, 83(18):9296-9303; Massin et al, 2005, J Virol, 79(21):13811-13816; Murakami et al, 2008, 82(3):1605-1609; Koudstaal et al, 2009, Vaccine, 27(19):2588-2593; Schickli et al, 2001, Philos Trans R Soc Lond Biol Sci, 356(1416):1965-1973; Nicolson et al, 2005, Vaccine, 23(22):2943-2952; Legastelois et al, 2007, Influenza Other Respi Viruses, 1(3):95-104; Whiteley et al, 2007, Influenza Other Respi Viruses, 1(4):157-166.

Preferably, said methods may be:

(i) the 16 plasmid method, such as the method described by Neuman et al, 1999, Proc Natl Acad Sci USA, 96(16):9345-9350, and in US 2009/0246830 or US 2011/0143424, in which the influenza virus is produced by transfecting cells, using a polyamine derivative (Trans IT-LT1), with 8 plasmids each containing a cDNA complementary to one influenza vRNA under the control of an RNA polymerase I promoter and an RNA polymerase I terminator, and 8 plasmids each containing a cDNA complementary to one of the PA, PB1, PB2, NP, HA, NA, M and NS mRNAs under the control of RNA polymerase II promoter. In particular, the cells are human kidney embryonic adherent cells (293T cell line);

(ii) the 12 plasmid method, such as the method described by Fodor et al, 1999, J Virol, 73(11):9679-9682, and in US 2004/0142003, US 2012/0058538 in which the influenza virus is produced by transfecting a first cell type with 8 plasmids each containing a cDNA complementary to one influenza vRNA under the control of an RNA polymerase I promoter and an RNA polymerase I terminator (hepatitis delta ribozyme), and 4 plasmids each containing a cDNA complemetary to one of the NP, PA, PB1 and PB2 mRNAs under the control of RNA polymerase II promoter, and by further amplifiying the virus on a second cell type. In particular, said first cell type is Vero cells and said second cell type is MDBK;

(iii) the 13 plasmid method, such as the method described by De Wit et al, 2007, Journal of General Virology, 88:1281-1287 in which the influenza virus is produced by transfecting cells with 8 plasmids each containing a cDNA complementary to one influenza vRNA under the control of an T7 RNA polymerase promoter and an T7 RNA polymerase terminator, 4 plasmids each containing a cDNA complementary to one of the NP, PA, PB1 and PB2 mRNAs under the control of RNA polymerase II, and one plasmid containing the cDNA complementary to the mRNA encoding the T7 RNA polymerase and a nuclear localization signal under the control of RNA polymerase II. In particular, the transfected cells are Vero, 293T, or QT6 (fibrosarcoma cell line from Japanese quail) cells.

(iv) the 8 plasmid method, such as the method described by Hoffmann et al, 2000, PNAS, 97(11):6108-6113 and in WO 01/83794 in which each plasmid is capable of expressing both mRNA and vRNA(s). Thus each plasmid contains cDNA complementary to one influenza vRNA and two transcription cassettes instead of one as in the preceding case. The cDNA complementary of each of the eight influenza virus vRNAs is inserted between the polymerase I terminator and the polymerase I promoter. This polymerase I transcription unit is flanked by the polymerase II promoter and a polyadenylation signal. The first transcription cassette allows the transcription of cDNA in the form of a vRNA. The second transcription cassette allows the transcription of cDNA in the form of mRNA which is then translated into viral protein(s) using the cellular machinery. With the aid of this double cassette system for transcription, also called Pol I-Pol II system, the cDNA of the same plasmid is transcribed both in the form of vRNA and in the form of mRNA. This manifests itself at the level of the transfected cell by the expression of a vRNA and of one or more viral proteins. In particular, a co-culture of adherent MDCK cells and of 293T cells and, as transfection agent, a polyamine derivative (Trans IT-LT1) are used.

(v) the 3 plasmid method, such as the method described by Neumann et al, 2005, PNAS, 102(46): 16825-16829, in which the influenza virus is produced by transfecting cells with one plasmid containing the 8 cDNAs complementary to PB2, PB1, PA, HA, NP, NA, M and NS vRNAs each under the control of an RNA polymerase I promoter and a polymerase I terminator and 2 plasmids, the first one containing the 3 cDNA complementary to one of the PB2, PB1 and PA mRNAs and the second one containing the cDNA complementary to the NP mRNA, under the control of a RNA polymerase II promoter. In particular, the transfected cells are 293T or Vero.

(vi) the 1 plasmid method, such as the method described by Zhang et al, J. Virol., 83(18): 9296-9303, in which the influenza virus is produced by transfecting cells with one plasmid containing the 8 cDNAs complementary to PB2, PB1, PA, HA, NP, NA, M and NS vRNA under the control of murine polymerase I terminator and a chicken RNA polymerase I promoter and with a polymerase II promoter and a polyadenylation signal between PB2, PB1, PA and NP cDNAs. In particular, the transfected cells are CEF cells.

(vii) the method described in WO 2005/062820 using two different cellular systems: in a first step, cells are transfected with 8 bidirectional plasmids with the PolI-PolII system (Pol/PolI) and then in a second step, the transfected cells are cultured with cells from another cell line that is very permissive for the influenza virus in order to amplify the production of the influenza virus. In particular, said transfected cells in the first step are Vero cells, and said other cell line in the second step are CEK or CEF cell lines which are lines derived from chicken embryo cells.

"Influenza virus proteins" denotes the PB1, PB2, PA, HA, NP, NA, M1, M2, NS1 and NS2/NEP proteins for type A influenza, PB1, PB2, PA, HA, NP, NA, NB, M1, BM2, NS1 and NS2/NEP proteins for type B influenza, or PB1, PB2, PA, HEF, NP, M1, M1', CM2, NS1 and NS2/NEP for type C influenza.

By "influenza virus proteins necessary to form the ribonucleoprotein complex" is meant the proteins PA, PB1, PB2 and NP for type A, B or C influenza virus.

By "vRNA" is meant the negative-sense viral RNA of the influenza virus which is encapsulated into the ribonucleoprotein complex. When the influenza virus is of type A or B, said vRNAs are PB2, PB1, PA, HA, NP, NA, M and NS vRNAs. When the influenza virus is of type C, said vRNAs are PB1, PB2, PA, HEF, NP, M and NS vRNAs.

By "cRNA" is meant the positive-sense RNA intermediate which is complementary to the vRNA. Once in the nucleus, the incoming negative-sense viral RNA (vRNA) is transcribed into messenger RNA (mRNA) by a primer-dependent mechanism. These mRNA products are incomplete copies of the vRNA template and are capped and polyadenylated, unlike vRNA. Replication occurs via a two-step process. A full-length, positive-sense copy of the vRNA is first made that is referred to as complementary RNA (cRNA) and is in turn used as a template to produce more vRNA.

Recombinant Cassette, Vectors and their Uses

An aim of the present invention is to provide a novel recombination cassette that can be used for cloning cDNAs complementary to vRNAs of a negative single-stranded RNA virus into an expression vector. Said recombination cassette is thus particularly useful for cloning cDNAs complementary to vRNAs of type A and type B influenza viruses.

The invention thus relates to a recombination cassette comprising, or consisting of, in the 5' to 3' sense:
   an inverted complementary recognition sequence for a first restriction enzyme which has its cutting site outside of its recognition sequence and produces sticky ends;
   a restriction site for a second restriction enzyme which has its cutting site inside of its recognition sequence;
   a restriction site for a third restriction enzyme which has its cutting site inside of its recognition sequence; and
   a recognition sequence for said first restriction enzyme which has its cutting site outside of its recognition sequence and produces sticky ends;
wherein said second and third restriction enzymes are different.

A "restriction enzyme" denotes an endonuclease that binds to a recognition site and then cleaves a DNA strand at a fixed position relative to its recognition sequence (type II restriction enzyme). The "recognition sequence" is the specific nucleotide sequence to which a restriction enzyme binds prior to cutting the DNA backbone. Recognition sequences are generally 4 to 8 base pairs in length, and are often palindromic—that is, they read the same backwards and forwards when they are read in the 5'-3' direction—, and the recognition sequence is often the same on both strands of the DNA. The "cutting site" is the specific nucleotide sequence at which the restriction enzyme cuts. In some cases, the cleavage points occur exactly on the axis of symmetry of the palindromic restriction site, giving products which are blunt-ended. Some restriction nucleases produce staggered cuts, which leave short single-stranded tails at the two ends of each fragment, known as "cohesive ends" or "sticky ends".

Positions of cleavage relative to the recognition sequence depend on the enzyme. For instance, for the SapI or BbsI enzymes (type IIS restriction enzyme), the cutting site is outside of the recognition sequence:

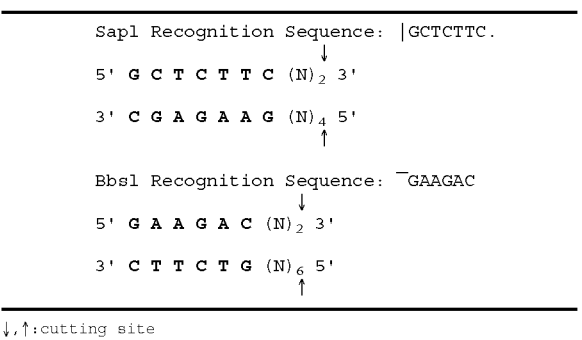

↓,↑:cutting site

As used herein a "restriction site" preferably denotes a nucleotide sequence which consists of the recognition sequence for a restriction enzyme and which contains the cutting site of said enzyme.

In some embodiments, said first restriction enzyme having its cutting site outside of its recognition sequence may be BbsI, SapI, AceIII, BsaI, or BsmB1.

Preferably, said first restriction enzyme is BbsI or SapI. Consequently, when the first restriction enzyme is BbsI, said inverted complementary recognition sequence consists of the sequence 5'-GTCTTC-3', said BbsI recognition sequence consisting of the sequence 5'-GAAGAC-3'. When the first restriction enzyme is SapI, said inverted complementary recognition sequence consists of the sequence 5'-GAAGAGC-3', said SapI recognition sequence consisting of the sequence 5'-GCTCTTC-3'.

In order to minimize the risk of having the second and third restriction sites present in the viral genome, said restriction sites preferably have a long nucleotide sequence. In some embodiments, the restriction site of said second and third restriction enzymes is at least, or exactly, 7, 8, 9, 10, 11, 12, 13, 14, 15, 16, 17, 18, 19, or 20 nucleotides-long. Preferably, the restriction site of said second and third restriction enzymes is at least, or exactly, 7 or 8 nucleotides-long.

In some embodiments, said second and third restriction enzymes are selected from the group consisting of NotI and SbfI. Still preferably, said second restriction enzyme is NotI and said third restriction enzyme is SbfI.

Consequently, the restriction site of the second or third restriction enzyme may consists of the sequence 5'-GCGGCCGC-3' or of the sequence 5'-CCTGCAGG-3'. Preferably, the restriction site of the second restriction enzyme consists of the sequence 5'-GCGGCCGC-3', and the restriction site of the third restriction enzyme consists of the sequence 5'-CCTGCAGG-3'.

The recombination cassette may comprise additional nucleotides between said inverted and complementary recognition sequence for a first restriction enzyme and said restriction site for a second restriction enzyme; and/or between said restriction site for a second restriction enzyme and said restriction site for a third restriction enzyme. In some embodiments, said additional nucleotides may consist of a stretch of at least 1, 2, 3, 4, 5, 6, 7, 8, 9, 10, 15, 20, 25, 30 nucleotides. In some embodiments, said additional nucleotides consist of a stretch of at most 1, 2, 3, 4, 5, 6, 7, 8, 9, 10, 15, 20, 25, 30 nucleotides.

Consequently, said recombination cassette is at least, or exactly, 20, 21, 22, 23, 24, 25, 26, 27, 28, 29, 30, 35, 40, 45, 50, 55, 60, 65, 70, 75, 80, 85, 90, 95, 100, 105, 110, 115, 120 nucleotide-long. Preferably, said recombination cassette is at least, or exactly, 28 or 30 nucleotide-long.

Preferably, said recombination cassette consists of the sequence 5'-GTCTTCGCGGCCGCCCTGCAGGGAAGAC-3' (SEQ ID NO: 2).

It has to be understood that said recombination cassette is double-stranded nucleic acid, and that the sequences described hereabove corresponds to the coding strand of the nucleic acid.

The invention also relates to a vector comprising, in the 5' to 3' sense:
a promoter that binds to RNA polymerase I, or a T7 RNA polymerase,
the recombination cassette according to the invention,
a terminator sequence,
it being understood that:
when the promoter binds to RNA polymerase I, said terminator sequence is hepatitis delta ribozyme sequence, and
when the promoter binds to T7 RNA polymerase, said terminator sequence is the T7 polymerase terminator sequence.

By "terminator sequence" is meant a sequence that marks the end of gene or operon on DNA for transcription. Said hepatitis delta ribozyme sequence comprises, or consists of, sequence SEQ ID NO: 3. Said T7 polymerase terminator sequence comprises, or consists of, sequence SEQ ID NO: 4.

In some embodiments, said promoter binds to a rodent RNA polymerase I or to a human RNA polymerase I. Preferably, said promoter binds to a mouse or hamster RNA polymerase I.

In some embodiments, said promoter which binds to rodent RNA polymerase I comprises, or consists of the sequence SEQ ID NO: 5, SEQ ID NO: 6 or SEQ ID NO: 7.

In some embodiments, said promoter that binds to human RNA polymerase I comprises or consists of the sequence SEQ ID NO: 8.

Preferably, said vector comprises in the 5' to 3' sense:
a promoter that binds to human RNA polymerase I,
the recombination cassette of sequence SEQ ID NO:2,
the hepatitis delta ribozyme sequence of sequence SEQ ID NO:3.

More preferably, said vector comprises the sequence SEQ ID NO: 1.

Still preferably, said vector comprises in the 5' to 3' sense:
a promoter that binds to rodent RNA polymerase I,
the recombination cassette of sequence SEQ ID NO:2,
the hepatitis delta ribozyme sequence of sequence SEQ ID NO:3.

Still preferably, said vector comprises in the 5' to 3' sense:
a promoter that binds a T7 polymerase of sequence SEQ NO:9,
the recombination cassette of sequence SEQ ID NO:2,
the T7 polymerase terminator of sequence SEQ ID NO:4.

In the vector according to the invention, said recombination cassette is preceded by the promoter that binds to RNA polymerase I, or to T7 RNA polymerase, and is immediately followed by the terminator sequence.

In some embodiments, said vector may also comprise an antibiotic resistance gene, such as the kanamycine resistance gene. Accordingly, said vector comprises or consists of the sequence SEQ ID NO:10, i.e. said vector is the so-called universal pSP-flu plasmid.

In some embodiments, the vector according to the invention does not comprise any antibiotic resistance gene, but comprises an antibiotic-free selection system, such as the system described in Peubez et al, 2010, Microbial Cell Factories, 9:65.

The vector according to the invention may be used in a method for producing negative single-stranded RNA viruses, in particular infectious negative single-stranded RNA viruses, by reverse genetics. In particular, said vector may be used for cDNA complementary to vRNA.

For example, said negative single-stranded RNA virus may be a virus of the Arenaviridae family, such as the Lymphocytic choriomeningotis virus; the Orthomyxoviridae family, such as an Influenza virus, an Isavirus, and a Thogotovirus; the Paramyxoviridae family, such as the Measle virus, the Mumps virus, the Respiratory syncytial virus, the Rinderpest virus, and the Canine distemper virus; the Bunyaviridae family, such as the California encephalitis virus, and the Hantavirus; the Rhabdoviridae family, such as the Rabies virus; the Filoviridae family, such as the Ebola virus, and the Marburg virus; the Bornaviridae family, such as the Borna disease virus.

Preferably, said negative single-stranded RNA virus may be a reassortant virus and/or chimeric virus. These viruses can be attenuated virus, or inactivated virus. In a particular preferred embodiment, said negative single-stranded RNA virus is an influenza virus.

Methods for producing negative single-stranded RNA virus by reverse genetics are well known by the one skilled in the art. For example, said method is a method for producing the VSV virus as described in Pattnaik et al, 1992, Cell, 69(6):1011-1020; the Rabies virus as described in Schnell et al, 1994, EMBO J, 13(18):4195-4203; the Measles virus as described in Radecke et al, 1995, EMBO J, 14(23):5773-5784; the Sendai virus as described in Garcin et al, 1995, EMBO J, 14(24):6087-6094; the Parainfluenza type 3 virus as described in Hoffman and Banerjee, 1997, J Virol, 71(6):4272-4277 and in Durbin et al, 1997, Virology, 235(2):323-332; the SV5 virus as described in He et al, 1997, Virology, 237(2):249-260; the Rinderpest virus as described in Baron and Barrett, 1997, J Virol, 71(2):1265-1271; the RSV virus as described in Jin et al, 1998, Virology, 251(1):206-014; the Newcastle virus as described in Peeters et al, 1999, J Virol, 73(6):5001-5009; the Ebola virus as described in Neumann et al, 2002, J Virol, 76(1):406-410; the Parainfluenza type 2 virus as described in Kawano et al, 2001, Virology, 284(1):99-112; the Metapneumovirus as described in Herfst et al, 2004, J Virol, 78(15):8264-8270; the Bunyamwera virus as described in Bridgen and Elliott, 1996, Proc Natl Acad Sci USA, 93(26):15400-15404.

Preferably, said method for producing negative single-stranded RNA virus by reverse genetics is a method for producing influenza virus as described hereabove. More preferably, said method producing influenza virus may be the method described in Neuman et al, 1999, Proc Natl Acad Sci USA, 96(16):9345-9350, US 2009/0246830, US 2011/0143424, Hoffmann et al, 2002, Vaccine, 20(25-26):3165-3170, WO 01/83794, Fodor et al, 1999, J Virol, 73(11): 9679-9682, in US 2004/0142003, US 2012/0058538, De Wit et al, 2007, Journal of General Virology, 88:1281-1287, in WO 2005/062820, or the method according to the invention. Still preferably, said vector is used in the method according to the invention.

The vector according to the invention may be used in said methods after cDNAs complementary the vRNAs viruses have been cloned into one or more said vector(s).

Cloning Strategy

In the context of the invention, the cloning strategy involves homologous recombination between the vector according to the invention and the cDNA sequence to be cloned.

Thus, the invention further provides a method of cloning a cDNA complementary to a vRNA of a RNA virus which comprises the following steps:
(i) producing a cDNA complementary to a vRNA of the RNA virus by RT-PCR (reverse transcription-polymerase chain reaction) of viral RNA of the virus using a forward primer containing nucleotides from the promoter sequence of the vector according to the invention, and a reverse primer containing nucleotides from the terminator of the vector according to the invention;
(ii) linearizing the vector according to the invention using the first restriction enzyme of the recombination cassette;
(iii) contacting the obtained cDNA at step (i) with the linearized vector obtained at step (ii) in conditions that allow the homologous recombination between the said cDNA with the said vector.

At step (i), the reverse transcription may be performed by methods well-known by the one skilled in the art. Preferably, the reverse transcription is performed as described in the paragraph 1.8 of the examples.

In some embodiments, said reverse primer comprises, on its 5' side, at least 17 nucleotides from the terminator sequence of the vector according to the invention. Preferably, said reverse primer comprises, on its 5' side, at least 17 nucleotides from the hepatitis delta ribozyme sequence. Still preferably, reverse primer comprises, on its 5' side, the sequence 5'-CTGGGACCATGCCGGCC-3' (SEQ ID NO: 11). Said reverse primer further comprises, in 3' to the nucleotides from the terminator sequence, nucleotides complementary to the vRNA to be reverse transcribed.

In some embodiments, said forward primer comprises, on its 5' side, at least 17 nucleotides from the promoter sequence of the vector according to the invention. Preferably, said forward primer comprises, on its 5' side, at least 17 nucleotides from the promoter that binds a human RNA polymerase I. Still preferably, said forward primer comprises, on its 5' side, the sequence 5'-TGGGCCGCCGGGT-TATT-3' (SEQ ID NO: 12). Said forward primer further comprises, in 3' to the nucleotides from the promoter sequence, nucleotides complementary to the vRNA to be reverse transcribed.

Step (ii) may be performed by methods well-known by the one skilled in the art. Preferably, step (ii) is performed as described in the paragraph 1.8 of the examples.

Step (iii) may be performed by methods well-known by the one skilled in the art. Preferably, step (iii) is performed as described in the paragraph 1.8 of the examples.

Due to the use of said forward and reverse primers at step (ii), the obtained cDNA comprises, in the 5' to 3' sense, a nucleotide sequence from the promoter that binds to human polymerase I, the cDNA encoding a vRNA of a virus and a nucleotide sequence from the hepatitis delta ribozyme sequence. Consequently, at step (iii) the obtained cDNA at step (i) is cloned in antisens into the vector according to the invention.

In some embodiments, said cloning strategy further comprises a step (iv) consisting of eliminating the vectors that do not contain the obtained cDNA at step (i). Step (iv) may be performed by digesting the vectors that have been contacted with the obtained cDNA at step (iii) with the second and third restriction enzymes described in the paragraph "Recombinant cassette, vectors and uses", e.g. by using the NotI and SbfI enzymes, in appropriate conditions, if the recombination cassette included NotI and SbfI restriction sites. Said appropriate conditions are well-known by the one skilled in the art.

Thanks to the features of the vector according to the invention, this cloning strategy can be carried out to insert the cDNA complementary to a vRNA from type A as well as type B influenza viruses. The vector according to the invention represents an improved tool over the prior art as it allows the cloning of a cDNA complementary to vRNA from both type A and type B Influenza viruses.

Method for Producing Infectious Influenza Viruses

In order to sustain a high yield of influenza production, cells must express Sia2-6Gal or Sia2-3Gal receptors on their surface. Although CHO-K1 cells do not express Sia2-6Gal receptors and express only poorly Sia2-3Gal receptors (expressed in 30% of the cells), it has been surprisingly found that the CHO-K1 cell line, which is a subclone of the CHO cell line is a very efficient cell line for the production of influenza virus which has been generated by molecular biology, in particular by reverse genetic methods by means of an appropriate set of expression vectors.

Accordingly the invention relates to a method for producing infectious influenza viruses, according to which the proliferation (amplification) of the virus is achieved by infecting CHO cells with a seed of infectious influenza viruses obtained by reverse genetics using a set of expression vectors capable of generating infectious influenza virus, and the method for producing infectious influenza viruses thus involves a preliminary step according to which cells are transfected with said set of expression vectors. The supernatant of transfected cell-containing medium becomes infectious, can be harvested and used as infectious seed to infect a separate population of CHO cells. Alternatively, after the transfection step, CHO cells can be added in situ to the transfected cells to allow the proliferation of influenza viruses.

The subject matter of the invention is therefore a method for producing infectious influenza viruses ("reverse genetics method"), wherein said method comprises the steps comprising or consisting of:
  a) transfecting cells with a set of expression vectors to generate a seed of infectious influenza viruses,
  b) infecting CHO cells with said seed of infectious influenza viruses.

In the method according to the invention, the seed of infectious influenza viruses is obtained by transfecting cells with a set of expression vectors capable of generating said infectious viruses.

Usually, step b) of infecting CHO cells is performed by adding CHO cells to the cells transfected with the set of expression vectors capable of generating said infectious viruses (the "transfected cells"), thereby allowing the proliferation of infectious viruses that have been generated. Step b) of infecting CHO cells could also be performed by adding the seed of infectious influenza viruses generated at step a) to CHO cells.

It is well understood that the infection a CHO cells with said seed of infectious influenza viruses is made under culture conditions well known by the skilled in the art that allow the proliferation of infectious influenza virus. The proliferation of the infectious influenza virus can be further amplified by successive infections of CHO cell populations or any other highly permissive cell populations, or by infecting the allantoïc cavity of embryonated hen's eggs.

The production of infectious influenza viruses is achieved by ex vivo or in vitro infecting CHO cells with said seed of infectious influenza viruses in conditions that are well known by the one skilled in the art. For instance, said infection can be performed at a temperature comprised between 32 and 38° C., or more usually between 34° C. and 37° C., and with 5% to 10% $CO_2$. As a matter of specific example, the infection can be carried out at about 35° C. with about 8% $CO_2$. Generally, trypsin or an enzyme having a serine protease activity is added into the medium to allow the virus to replicate into cells and to ensure the propagation of the influenza viruses through the CHO cells.

In a particular preferred embodiment, infection of CHO cells with said seed of infectious influenza viruses is performed in an infection medium which is a serum free medium. Preferably, said method for producing infectious influenza viruses is performed entirely in the absence of serum.

Preferably the method according to the invention is carried out in the absence of a helper virus, which means that the use of an appropriate set of expression vectors alone is enough to allow the generation of infectious influenza viruses by reverse genetics.

According to the structural features of the expression vectors used, the cells or cell line(s) used for the transfection step can comprise or consist of a CHO cell line, a mixture of a CHO cell line with another cell line, or a cell line that is not a CHO cell line.

When the method according to the invention is carried out by reverse genetics using a set of expression vectors comprising plasmids for vRNA production under the control of promoter that binds to human RNA polymerase I, preferably the cells used for transfection are cells of primate origin or preferably a mixture of cells of primate origin and CHO cells. The cells of primate origin can be for instance PER.C6® cells (Crucell), 293 T cells or Vero cells. Typically, the cells used for transfection are Vero cells or preferably a mixture of Vero cells and CHO cells.

In the same way, when the plasmids for vRNA production contain a promoter that binds to canine or avian RNA polymerase I (Massin et al, 2005, J Virol, 79(21):13811-13816; Murakami et al, 2008, 82(3):1605-1609), preferably the cells used for transfection are respectively cells of canine origin, such as MDCK cells (or preferably a mixture of cells of canine origin and CHO cells) or chicken cells, such as CEF cells or CEP cells (or preferably a mixture of cells of chicken origin and CHO cells).

Lastly when the plasmids for vRNA production contain a promoter that binds to rodent RNA polymerase I such as a Hamster or a mouse RNA polymerase I, the transfection step can be carried out using only CHO cells. In that case, CHO cells are the only type of cells to be used for both transfection and infection steps. Therefore, the production of infectious influenza viruses from an appropriate set of expression vectors may only involves the use of CHO cells, which simplifies the influenza virus production process. Only one cell line has to be cultivated.

Alternatively when the appropriate set of expression vectors comprise plasmids for vRNA production under the control of the T7 polymerase promoter and an additional protein expression plasmid encoding the T7 polymerase as described by De Wit et al, 2007, J. Gen. Virol, 88 (Pt4): 1284-1287, CHO cells can be also the only type of cells to be used for both transfection and infection steps and to ensure the production of infectious influenza viruses.

In some embodiments the cells used for transfection (for instance CHO cells or a mixture of Vero cells and CHO cells) can be recombinant cells stably expressing influenza PB2, PB1, PA and NP proteins and the set of vectors to be incorporated in the recombinant cells are a set of expression vectors capable of expressing PB1, PB2, PA, NP, M, NS, HA and NA vRNAs.

Thus in some embodiments, said cells at step a) comprise or consist of Vero cells or a mixture of Vero cells and CHO cells.

In some embodiment also, said cells at step a) comprise or consist of CHO cells.

The cell line for use according to the invention is a CHO cell line. CHO cell lines are commonly used for industrial protein production and many CHO cell lines are known to the skilled person in the art. For instance, such CHO cell lines include, e.g. the CHO-K1 cell line available on the ATCC catalogue under the number CCL-61 or CCL-9618, the CHO DP-12 cell line (ATCC Number: CRL-12444 and 12445) and the CHO 1-15 cell line (ATCC Number CRL-9606). According to an embodiment, the cell line used for the purpose of the invention is a CHO cell line which does not express on its surface the Sia2-6Gal receptors, but express weakly the Sia 2-3Gal receptors such that less than 50% of the cell population is fluorescent in presence of the digoxigenin-labeled Maackia amurensis agglutinin. Preferably the cell line used for the purpose of the invention is the CHO-K1 cell line, in particular the cell line referenced at the ATCC under the number CCL-61. Still preferably the CHO-K1 cell line, for instance the CHO-K1 cell line referenced at the ATCC under the number CCL-61, is in the form of a suspension of cells. For example, such suspension of cells can be obtained by cultivation of the cell line in a serum-free medium.

When a primate cell line is used in combination with a CHO cell line to carry out the method according to the invention, Vero cell lines available on the ATCC catalogue under the number CCL-81, CRL-1586, CRL-1587 or CCL-81.5 are preferred since they were approved a long time ago by the regulatory authorities. Preferred 293-T cell lines include the line available on the ATCC catalogue under the number CRL-11268.

CHO and transfected cells, in particular Vero cells, preferably are cultivated in accordance to the GLP (Good Laboratory Practices)/GMP (Good Manufacturing practices) regulations or the requirements of the national control authority. For example, said cells may be identified by historical records, i.e. information of the origin of the cells, its method of development, the in vitro culture age limit for production. Said cells may also be free of cultivable bacteria, mycoplasmas, fungi, endogenous viruses. guidance related to considerations for cell cultures and materials used to support cell cultures for vaccine production can be found in the who expert committee on biological standardization, 47th report, requirements for the use of animal cells as in vitro substrates for the production of biologicals (WHO technical report series, 1998, 878:19-52), in the characterization and qualification of cell substrates and other biological materials used in the production of viral vaccines for infectious disease indications (US department of health and human services food and drug administration center for biologics evaluation and research [February 2010]), in paragraph 5.2.3 of the European pharmacopoeia, $5^{th}$ edition, or in note for guidance on quality of biotechnological products: derivation and characterisation of cell substrates used for production of biotechnological/biological products (cpmp/ich/294/95) published by the European Medicines Agency.

CHO and the transfected cells, in particular Vero cells, are preferably adapted for culture in serum-free medium and/or animal component free conditions.

Cell adaptation to culture in serum free medium may readily achieved by the one skilled in the art by progressively passaging cells on media containing decreasing serum amounts, until the cells can successfully survive and proliferate in a serum-free medium.

When Vero cells or a mixture of Vero cells and CHO cells are used for transfection, Vero cells which are adherent are preferably detached from their support, for instance by treatment with trypsin prior to transfection to improve the efficacy of transfection. Accordingly, the transfection is preferably performed on a suspension of cells. The cells may however become adherent in the course of the method. Alternatively, one may also use a Vero cell line adapted to grow in suspension as described in US 2009/0203112, the subject of which is incorporated herein by reference.

In the frame of the methods according to the invention, transfection may be performed by any method known by the one skilled in the art. For example, transfection may be performed by membrane electroporation, nuclear electroporation. Preferably, transfection (step a)) is performed by nuclear electroporation. The expression "nuclear electroporation" is understood to mean a method of transfection of nucleic acids by means of one or more electric shocks whose intensity is sufficient to increase the number of nuclear pores and/or the permeability thereof. Generally, the total intensity of the electric shock(s) is at least 2 kV/cm and the total duration of the shock(s) is at least 10 µs. Nuclear electroporation of the cells in suspension is performed by means of one or more electric shocks whose total intensity is at least 2 kV/cm and for which the total duration of the shock(s) is at least 10 µs. Preferably, the total intensity of the shock(s) is between 2 and 10 kV/cm and the total duration of the shock(s) is between 10 and 1000 µs. Still more preferably, the intensity of the shock(s) is between 2 and 6 kV/cm and the total duration of the shock(s) is between 100 and 600 µs. Preferably, several electric shocks interrupted by one or more rest periods are delivered to the cells. US 2007/0059834 whose subject is incorporated herein by reference describes practical modes of administration of electric shocks to cells followed by periods of rest. Following the electric shock(s), it is also possible to apply to the cells an electric current whose intensity does not exceed 2.5 A and for a period of between 1 and 50 ms. Typically, the transfection step is performed as detailed in the paragraph 1.9. of the Examples, i.e. the transfection is performed using a nucleofector, such as the nucleofector marketed by Lonza using the U-023 program.

The transfection solution is chosen such that it protects the cells from electric shock(s) and such that it does not prevent the diffusion of the expression vectors towards the nuclei. US 2005/0064596 whose subject is incorporated herein by reference describes optimized transfection solution. They are formulations whose buffer capacity is at least 20 mM $pH^{-1}$ and which have ionic strengths of at least 200 mM when they are subjected to a temperature of 25° C. and at a pH variation ranging from 7 to 8. Preferably, the molar concentrations of $Na^+$ and $K^+$ in these formulations are between 100 and 150 mM and between 2 and 6 mM, respectively. They generally also contain $Mg^{++}$ ions. Transfection media which can be used in the context of the invention are given, by way of example:

Transfection solution No. 1: 4-6 mM KCl, 10-20 mM $MgCl_2$, 120-160 mM and $Na_2HPO_4/NaH_2PO_4$ (pH 7.2);

Transfection solution No. 2: 4-6 mM KCl, 10-20 mM $MgCl_2$, 5-25 mM HEPES,120-160 mM and $Na_2HPO_4/NaH_2PO_4$ (pH 7.2);

Transfection solution No. 3: 4-6 mM KCl, 10-20 mM MgCl$_2$, 50-160 mM Na$_2$HPO$_4$/NaH$_2$PO$_4$ (pH 7.2) and 5-100 mM of sodium lactobionate or 5-100 mM mannitol or 5-100 mM sodium succinate or 5-100 mM of sodium chloride;

Transfection solution No. 4: 4-6 mM KCl, 10-20 mM MgCl$_2$, 5-25 mM HEPES, 50-160 mM Na$_2$HPO$_4$/NaH$_2$PO$_4$ (pH 7.2) and 5-100 mM of sodium lactobionate or 5-100 mM mannitol or 5-100 mM sodium succinate or 5-100 mM of sodium chloride;

Transfection solution No. 5: 4-6 mM KCl, 10-20 mM MgCl$_2$, 80-100 mM NaCl, 8-12 mM glucose, 0.3-0.5 mM Ca(NO$_3$)$_2$, 20-25 mM HEPES and 50-100 mM tris/HCl or 30-50 mM Na$_2$HPO$_4$/NaH$_2$PO$_4$ (pH 7.2);

Transfection solution No. 6: 0.1-3.0 mM MgCl$_2$, 50-200 mM K$_2$HPO$_4$/KH$_2$PO$_4$ (pH 6.5) and/or 1-50 mM mannitol and/or 1-50 mM of sodium succinate; and Transfection solution No. 7: 0.42 mM Ca(NO$_3$)$_2$; 5.36 mM KCl; 0.41 mM MgSO$_4$; 103 mM NaCl; 23.8 mM NaHCO$_3$; 5.64 mM Na$_2$HPO$_4$; 11.1 mM d(+)-glucose; 3.25 µM glutathione; 20 mM HEPES; pH 7.3;

Phosphate Buffer Saline (PBS).

Still preferably the electroporation solution is the solution V provided by Lonza in the kit referenced as Amaxa™ Cell line Nucleofector Kit V-VCA-1003.

Consecutive to the transfection step, a culture medium is added to the transfected cells in a ratio of at least 5 volumes of culture medium for 1 volume of transfection solution, preferably 10 volumes, still preferably 15 volumes of culture medium for 1 volume of transfection solution. Preferably the culture medium is a medium suitable for the culture of CHO cells. A medium suitable for both CHO cells and Vero cells or a mixture of a medium suitable for CHO cells and a medium suitable for Vero cells can also be used when Vero cells are used during the transfection step.

In particular, the transfection is performed as described in the paragraph 1.9 of the examples.

The medium used during the infection step (infection medium) can be any medium suitable for the culture of CHO cells. Even if some infectious influenza viruses can proliferate to some extent in CHO cells in an infectious medium without trypsine, very preferably it contains or it has been added trypsin or an enzyme having a serine protease activity to allow the virus to replicate into cells and to ensure the propagation of the influenza viruses through the other CHO cells. Indeed, the hemagglutinin of influenza viruses must be cleaved by a serine protease for the virus to be able to replicate into the cells. Preferably, Trypsin is of synthetic origin or is free of any product of animal origin. Trypsin or more generally any enzyme having a serine protease activity such as pronase, subtilisin, plasmin, or thermolysin can be produced by genetic recombination. Trypsin may be produced in particular by means of transgenic plants (WO 00/05384), yeasts or bacteria (WO 01/55429). For instance, a recombinant trypsin provided by Gibco under the trade name TrypLE Select or by Invitrogen under the trade name TrypLE Express is suitable for the purpose of the invention.

Preferably the media used in the context of the invention, including culture medium and infection medium are free of serum of animal origin, preferably are free of any protein of animal origin and still more preferably are free of any component of animal origin. Examples of media free of serum of animal origin and/or free of raw material of animal origin which may be suitable for the subject of the invention are marketed under the names VP SFM (InVitrogen), Episerf (InVitrogen), LC17 (Cambrex), Pro CHO 5-CDM (Cambrex), HyQ SFM4CHO (Hyclone), HyQ SFM4CHO-Utility (Hyclone), HyQ PF Vero (Hyclone), Ex cell 325 PF CHO Protein free medium (JRH Biosciences), Ex cell 302 serum free medium (JRH Biosciences), Excell 525, Ex Cell™ CD CHO Fusion (SAFC Biosciences). It is therefore possible to carry out the method according to the invention using animal free media (e.g. which are free of any contaminant or component of animal origin). In particular a medium suitable for the subject of the invention is the Ex Cell™ CD CHO Fusion medium manufactured by SAFC Biosciences supplemented with L-Glutamine. To produce infectious influenza virus by CHO cell infection, trypsin or a trypsin derivative, preferably free of any component of animal origin, is added to this medium.

In some embodiments, the total amount of cells subjected to transfection is for instance 0.5, 1, 1.5, 2, 2.5, 3, 6 or even 10 millions of cells, or more.

In a further embodiment, when the cells subjected to transfection are a mixture of Vero cells and CHO cells, the Vero and CHO cells may be present in a Vero:CHO ratio ranging from 0.5:1 to 2:1, for instance of 1:1, 1.5:1, 1:0.5, or 1:1.5. Typically said Vero:CHO cell ratio is of 1:1. For instance, when said Vero:CHO cell ratio is of 1:1, the amount of cells of each type represents, for instance, at least 0.5, 1, 1.5, 2, 2.5, 3 millions of cells.

In some embodiments, the amount of CHO cells that are added after the transfection step for carrying out the infection step is for instance, at least 0.5, 1, 1.5, 2, 2.5, 3 millions of cells.

In some embodiments of the method of the invention, the expression vectors comprises expression vectors that allow the expression of both one or more influenza proteins and one or more influenza vRNAs, it being understood that expression of said set of expression vectors allows (i) the formation of the ribonucleoprotein complex (RNP) containing the vRNAs of said virus, and (ii) the assembling of said viral particles in said transfected cells. Optionally, Helper virus may be added to said set of expression vectors.

Such vectors are for instance bidirectional plasmids that promote the expression of both mRNAs and vRNAs each plasmid containing:

one or more cDNAs complementary to one or more of the eight vRNAs selected among influenza PB1, PB2, PA, NP, M, NS, HA and NA vRNAs, or the corresponding cRNA(s), wherein each cDNA is under the control of a promoter that binds to RNA polymerase II (POL II promoter), thereby allowing the expression of the corresponding influenza proteins, and of a promoter that binds to RNA polymerase I (POL I promoter), thereby allowing the expression of the corresponding vRNAs, or said corresponding cRNAs.

In some embodiments, the promoter that binds to RNA polymerase II is a promoter that binds to human RNA polymerase II and/or the promoter that binds to RNA polymerase I is a promoter that binds to human RNA polymerase I.

Preferably, if the set of expression vectors is transfected into CHO cells, the promoter that binds to RNA polymerase I is a promoter that binds to a rodent RNA polymerase I. The promoter that binds to rodent RNA polymerase I preferably binds to hamster or mouse RNA polymerase I.

In some embodiments, the set of expression vectors that allow the expression of both mRNAs and vRNAS, or the corresponding cRNAs, comprises one, two, three, four, five, six, seven, eight bidirectional plasmids as defined hereinabove. Preferably, said expression vectors consists of eight bidirectional plasmids, each plasmid containing a cDNA complementary to one of the eight vRNAs selected among influenza PB1, PB2, PA, NP, M, NS, HA and NA vRNAs, or the corresponding cRNA(s). Preferably, said expression vectors consist of the eight plasmids described in Ozawa et al, 2007, J Virol, 81(17):9556-9559.

The set of expression vectors may also comprises:
expression vectors that allow the expression of only one or more mRNAs encoding one or more influenza proteins, and
expression vectors that allow the expression of only one or more influenza vRNAs or the corresponding cRNAs, of the influenza virus, it being understood that expression of said set of expression vectors allows (i) the formation of the ribonucleoprotein complex (RNP) containing the vRNA of said virus, and (ii) the assembling of said viral particles in said transfected cells.

The vectors that induce the expression of only influenza proteins shall at least induce the expression of PB1, PB2, PA and NP proteins but may also induce the expression of the other influenza proteins (M, NS, HA and NA proteins). Preferably, said expression vectors are unidirectional plasmids, each plasmid containing one or more cDNAs inducing the expression of at least one or more proteins selected among the group of PB1, PB2, PA and NP proteins, wherein each cDNA is under the control of a promoter that binds to RNA polymerase II. Accordingly, said expression vectors may comprise the plasmids described in Fodor et al, 1999, J Virol, 73(11):9679-9682, or the pVAX1 plasmids, each cloned with the cDNA corresponding to one of the PB2, PB1, PA and NP proteins as described in paragraph 1.8 of the examples. Alternatively, the set of expression vectors comprise eight distinct plasmids, each plasmid containing one cDNA complementary to a mRNA encoding one distinct viral protein among PB1, PB2, PA, NP, M, NS, HA and NA proteins, under the control of a promoter that binds to RNA polymerase II. Accordingly, said expression vectors may comprise the eight plasmids described in Neumann et al, 1999, Proc Natl Acad Sci USA, 96(16):9345-9350.

The vectors that allow the expression of one or more influenza vRNAs or the corresponding cRNAs, shall induce the expression of influenza PB1, PB2, PA, NP, M, NS, HA and NA vRNAs, or the corresponding cRNAs. Preferably, said expression vectors are unidirectional plasmids, each plasmid containing one or more cDNAs complementary to one or more of said influenza PB1, PB2, PA, NP, M, NS, HA and NA vRNAs, or the corresponding cRNAs, each cDNA being under the control of a promoter that binds to RNA polymerase I. Said expression vectors may comprise at least one, two, three, four, five, six, seven or eight plasmids. Still preferably, said expression vectors that allow the expression of influenza PB1, PB2, PA, NP, M, NS, HA and NA vRNAs, or the corresponding cRNAs, comprise eight different plasmids, each plasmid containing one cDNA complementary to one of the eight vRNAs PB1, PB2, PA, NP, M, NS, HA and NA, under the control of a promoter that binds to RNA polymerase I. Accordingly, said set of expression vectors comprises the eight plasmids described in Neumann et al, 1999, Proc Natl Acad Sci USA, 96(16):9345-9350 or in Fodor et al, 1999, J Virol, 73(11):9679-9682. In another embodiment, the set of expression vectors that allow the expression of influenza PB1, PB2, PA, NP, M, NS, HA and NA vRNAs, or the corresponding cRNAs, is represented by one plasmid containing the 8 cDNAs complementary to PB1, PB2, PA, NP, M, NS, HA and NA vRNAs, each being under the control of an RNA polymerase I promoter and a polymerase terminator as described by Neumann et al, 2005, Proc Natl Acad Sci USA, 102(46):16825-16829. In another embodiment, the set of expression vectors that allows the expression of influenza PB1, PB2, PA, NP, M, NS, HA and NA vRNAs, or the corresponding cRNAs, comprise for instance two different plasmids, one plasmid containing six cDNAs, each of said cDNA being complementary to each of the PB1, PB2, PA, NP, M and NS vRNAs under the control of an RNA polymerase I promoter and one plasmid containing two cDNAs, each of said cDNA being complementary to each of the HA and NA vRNAs, each of the cDNA being under the control of a promoter that binds to RNA polymerase I. The plasmids containing one cDNA complementary to one of the eight PB1, PB2, PA, NP, M, NS, HA and NA vRNAs, or the corresponding cRNAs, under the control of a promoter that binds to RNA polymerase I are preferably obtained by cloning said cDNA into the vector comprising the sequence SEQ ID NO: 2. Still preferably, said each plasmid is obtained by cloning said cDNA into the vector comprising or consisting of the sequence SEQ ID NO: 10, i.e. into the universal pSP-flu plasmid.

In a particular preferred embodiment, the set of expression vectors comprises:
four different plasmids, each plasmid containing one cDNA complementary to a mRNA encoding one of the four viral PB2, PB1, PA and NP proteins under the control of a promoter that binds to RNA polymerase II, such as the plasmids described in Fodor et al, 1999, J Virol, 73(11):9679-9682, or the pVAX1 plasmids cloned with the cDNA encoding the PB2, PB1, PA and NP as described in paragraph 1.8 of the examples, and
eight different plasmids, each plasmid containing one cDNA complementary to one of the eight PB1, PB2, PA, NP, M, NS, HA and NA vRNAs, or the corresponding cRNAs, under the control of a promoter that binds to RNA polymerase I, said each plasmid being obtained by cloning said cDNA into the vector according to the invention, such as Universal pSP-flu plasmid.

Preferably vectors capable of expressing influenza PB1, PB2, PA, NP, M, NS, HA and NA vRNAs are vectors according to the invention in which PB1, PB2, PA, NP, M, NS, HA and NA cDNAs, respectively, have been cloned.

Vectors capable of expressing influenza PB1, PB2, PA and NP proteins may then be for instance the pVAX1 plasmid (Life technology, Cergy Pontoise, FR).

In another embodiment of the invention, the infectious influenza viruses produced according to the process of the invention may be a wild type influenza virus such as a seasonal or a pandemic influenza virus, a reassortant influenza virus, a chimeric influenza virus, or even an attenuated influenza virus.

Preferably, said infectious influenza virus that is produced according to the process of the invention is a reassortant influenza virus.

Still preferably, said infectious influenza virus is a reassortant chimeric influenza virus.

The infectious influenza viruses produced may be any subtype of A strains, B strains, or C strains. It can be a viral strain that infect human beings, such as A/H1N1, A/H3N2, A/H5N1, A/H7N1 or B strains. It can be a viral strain that infect birds such as A/H5N1, A/H5N2, A/H5N8, A/H5N9, A/H7N1, A/H7N3, A/H7N7 strains. It can be also a viral strain that infect horses (A/H3N8 strains), pigs (A/H1N1; A/H3N2 or A/H1N2 strains) and the like.

The infectious influenza viruses produced may be responsible for human seasonal influenza. In particular, said produced influenza virus according to the invention may be a A/H1N1, a A/H3N2 strain or a B Strain. It can also be a virus responsible for avian flu.

The infectious influenza viruses produced according to the invention could also be responsible for pandemic influenza. In particular, said produced influenza virus could be for instance a A/H1N1, a A/H5N1 or a A/H7N1 strain.

Preferably, the infectious influenza viruses are reassortant infectious influenza viruses, i.e. they contain genetic material that derives from at least two donor viruses.

Examples of type A reassortant viruses useful for the manufacturing of a type A influenza vaccine are of type 6:2 or 5:3 in which the respective 6 or 5 vRNAs are from a donor virus having good growth capacities on the production substrate, like A/PR/8/34 (H1N1), while the missing vRNA(s) are HA, NA segments and possibly the PB1 from a seasonal or pandemic virus. When the reassortant is a H1N1 virus of type 6:2 it may comprise the 6 vRNAs (PB1, PB2, PA NP, M, NS) from A/PR/8/34 (H1N1) virus and the HA and NA vRNAs from a seasonal or pandemic virus.

In particular, in the case of type A reassortant viruses of type 6:2, the 6 vRNAs segments may derive from the A/PR/8/34 (H1N1) virus and may comprise or consist of the PA vRNA of sequence SEQ ID NO: 13, the PB1 vRNA of sequence SEQ ID NO:14, the PB2 vRNA of sequence SEQ ID NO:15, the NP vRNA of sequence SEQ ID NO:16, the M vRNA of sequence SEQ ID NO:17, the NS vRNA of sequence SEQ ID NO:18.

A type B reassortant virus useful for the manufacturing of an influenza type B vaccine is for instance of type 2:2:4 (provided by New York Medical College) in which the PB2 and NP vRNAs are from the B/Lee/40 virus, the PA and NS vRNAd are from the B/Panama/45/90 virus and the HA, NA, PB1 and M vRNAs are from a seasonal B virus called B/Hubei-Wujiagang/158/209.

The infectious influenza viruses produced may also be chimeric influenza viruses, in particular chimeric reassortant influenza viruses and still more particularly said chimeric influenza virus contains a chimeric influenza HA and/or NA vRNAs.

In some embodiments, said HA or NA vRNA is chimeric.

Preferably, said chimeric influenza HA or NA vRNAs encodes a chimeric HA or NA protein. It comprises one or more domains of a HA vRNA or a NA vRNA fragment from a donor virus (such as A/PR8/34 (H1N1) or B/Lee/40) and one or more domains of a HA or NA vRNA from a seasonal or pandemic influenza virus In particular, said domain of HA vRNA of the seasonal or pandemic virus is complementary to a mRNA encoding the antigenic ectodomain of HA, such as HA1 and/or HA2 or said domain of NA vRNA of the seasonal or pandemic virus is complementary to a mRNA encoding the antigenic ectodomain of NA of said seasonal or pandemic virus.

For example, said chimeric HA vRNA contains the two NCR (Non-Coding Region) domains, the SP (Signal peptide) domain, the HA2 domain, the TM (Trans-Membrane) domain, and the Cyto (Cytoplasmic) domain derived from a donor virus, while the HA1 domain is derived from a seasonal influenza virus or a pandemic influenza virus.

Preferably, in the case of influenza virus type A, the chimeric HA vRNA contains the two NCRs, SP, HA2, TM and Cyto domains from the donor A/PR/8/34 (H1N1) virus, and the HA1 domain from a seasonal or pandemic influenza type A virus.

Still preferably, in the case of influenza virus type A, the chimeric HA vRNA contains the two NCRs, SP, HA2, TM and Cyto domains of respective sequences SEQ ID NO: 19, 20, 21, 22, 23 and 24 from the A/PR/8/34 (H1N1) donor virus, and the HA1 domain from a seasonal or pandemic influenza type A virus.

Preferably, in the case of influenza virus type B, the chimeric HA vRNA contains the domains NCRs, SP, HA2, TM, Cyto from a donor virus such as A/PR/8/34 (H1N1) or B/Lee/40, and the HA1 domain from a seasonal type B virus.

In the case of chimeric NA vRNA, it contains the NCRs, TM, Cyto and stalk domains derived from a donor virus, while the domain called ectodomain is derived from a seasonal or a pandemic influenza virus. Preferably, in the case of influenza virus type A, the chimeric NA vRNA contains the NCRs, TM, Cyto and Stalk domains from the A/PR/8/34 (H1N1) donor virus and the ectodomain from a seasonal or pandemic influenza virus. Still preferably, in the case of influenza virus type A, the chimeric NA vRNA contains the NCRs, TM, Stalk and Cyto domains of respective sequences SEQ ID NO: 25, 26, 27, 28 and 29 from the A/PR/8/34 (H1N1) donor virus and the ectodomain from a seasonal or pandemic virus. Preferably, in the case of influenza virus type B, the chimeric NA vRNA contains the NCRs, TM, Stalk and Cyto domains from a donor virus, such as A/PR/8/34 (H1N1) or B/Lee/40, and the ectodomain from a seasonal type B virus.

Host cells

The invention also relates to a CHO cell which comprises a set of expression vectors as defined hereabove.

Said CHO cell and infectious influenza virus are as described above.

Thus in particular said CHO cell is a CHO-K1 cell, as described above.

In a particular embodiment, said set of expression vector comprises:

(i) expression vectors capable of expressing influenza PB2, PB1, PA and NP proteins, and comprising four different plasmids, each plasmid containing one cDNA complementary to a mRNA encoding one of the viral proteins selected among PB2, PB1, PA and NP proteins under the control of a promoter that binds a RNA polymerase II, and (ii) expression vectors capable of expressing influenza PB1, PB2, PA, NP, M, NS, HA and NA vRNAs, or the corresponding cRNAs, and comprising eight different plasmids, each plasmid containing one cDNA complementary to one of the eight vRNAs selected among the PB1, PB2, PA, NP, M, NS, HA and NA vRNAs, or the corresponding cRNAs, under the control of a promoter that binds to rodent RNA polymerase I, and being obtained by cloning said cDNA sequence into a vector according to the invention, it being understood that said vector comprises a promoter that binds to rodent RNA polymerase I.

Said expression vectors capable of expressing influenza PB2, PB1, PA and NP proteins may comprise the plasmids described in Fodor et al, 1999, J Virol, 73(11):9679-9682, or the pVAX1 plasmids, each containing the cDNA complementary to a mRNA encoding one of the viral proteins selected among PB2, PB1, PA and NP as described in paragraph 1.8 of the examples.

Preferably, said vector according to the invention comprises a promoter that binds to hamster RNA polymerase I. Alternatively the promoter of the eight plasmids containing the cDNA complementary to the vRNAs is a T7 polymerase promoter. In that case the set of expression vectors contains an additional plasmid (total number is 13) containing a cDNA complementary to an mRNA encoding the T7 polymerase as described by De Wit et al, 2007, J. Gen. Virol, 88 (Pt4): 1284-1287.

The invention also relates to a recombinant CHO cell stably expressing influenza PB2, PB1, PA and NP proteins.

In a particular embodiment, such recombinant CHO cells may also contains a set of expression vectors capable of expressing influenza PB1, PB2, PA, NP, M and NS vRNAs.

Preferably, said recombinant CHO cell is a recombinant CHO-K1 cell.

Methods for establishing stable cells are well-known by the one skilled in the art. For example, said method is described by Wang et al, 2012, Genet Mol Res, 11(2):1442-1448 or by Liu et al., 2011, Sheng Wu Gong Cheng Xue Bao, 27(5):747-754.

Method for Preparing Pharmaceutical Compositions

The invention also relates to a method for preparing an influenza vaccine composition, which method comprises:

a) producing influenza viruses by a method according to any embodiment of the invention as previously described;
b) harvesting the infectious influenza viruses after multiplication in CHO cells, preferably in CHO-K1 cells,
c) purifying the harvested infectious influenza virus,
d) optionally inactivating the purified virus, and
e) mixing the purified virus with a pharmaceutically acceptable carrier.

The purification may be brief and may be limited to a step of concentrating the virus by centrifugation after having generally clarified the harvested infectious virus. The purification may be supplemented with centrifugation step carried out for example by means of sucrose density gradients (EP 0 7760362). Chromatographic methods may also be carried out in order to purify the virus. A suspension of purified whole viruses is thus obtained which can be further processed to get the final vaccine composition. The purified virus suspension may also undergo subsequent treatments. Flu virus-derived products are thus obtained. The viral suspension may be fragmented using detergents or lipid solvents according to methods well known to those skilled in the art, in order to manufacture, for example, vaccines based on fragmented or split viruses, virosomes, or subunit vaccines containing the flu virus hemagglutinin. The fragmented or split viruses, the virosomes containing the flu virus hemagglutinin and the subunit vaccines containing the flu virus hemagglutinin which are obtained from the purified virus are considered to be flu virus-derived products.

The final vaccine composition can be made up of whole inactivated flu virus or attenuated flu virus.

The inactivation of the viral suspension is carried out by conventional means, using β-propiolactone (E. Budowsky et al. 1991, Vaccine, 9: 319-325; 1991, Vaccine, 9: 398-402; 1993, Vaccine, 11: 343-348), ethyleneimine or derivatives (D. King 1991, Avian Dis. 35: 505-514) or formol (EP 0 776 0362). The inactivation of the virus can be carried out before or after the purification step.

The final vaccine composition is generally formulated with a pharmaceutically acceptable carrier.

By "pharmaceutically acceptable carrier" is meant any solvent, dispersing medium, charge, etc., commonly used on the formulation of pharmaceuticals and vaccines to enhance stability, sterility and deliverability of the active agent, which does not produce any secondary reaction, for example an allergic reaction, in humans. The excipient is selected on the basis of the pharmaceutical form chosen, the method and the route of administration. Appropriate excipients, and requirements in relation to pharmaceutical formulation, are described in "Remington's Pharmaceutical Sciences" (19th Edition, A. R. Gennaro, Ed., Mack Publishing Co., Easton, Pa. (1995)), which represents a reference work in the field. Examples of pharmaceutically acceptable excipients are water, phosphate-buffered saline solutions, 0.3% glycine solution.

The vaccinal composition based on inactivated whole viruses may also comprise one or more adjuvants. These vaccines may be formulated with aluminum salts, such as aluminium hydroxide gel, aluminium phosphate or alum, or in a water-in-oil or oil-in-water emulsion. Any adjuvant capable of increasing the humoral and/or cellular response against the flu may be used. As example of non limiting adjuvant formulations, mention is made of the MF59® emulsion, the liposome-based formulations, and formulations based on MPL, on *Corynebacterium parvum*, on saponin, on lysolecithin, on pluronic derivatives, or on combinations thereof. TLR agonists can also be used.

The vaccines obtained by means of the method according to the invention are for use in protecting humans and animals against the flu.

In the veterinary field, the vaccine is mainly used in the avian flu prevention field, but it may also be used for preventing or reducing flu symptoms and/or viral secretion in members of the equine family, in particular horses, members of the canine family, in particular dogs, members of the feline family, in particular cats, members of the porcine family, in particular pigs, mustelids, in particular minks and ferrets, and avian species, in particular hen, duck, turkey, quail, guinea-fowl, goose and ostrich In humans, the vaccine is used in the field of epidemic flu and pandemic flu prevention. While epidemic flu affects a human population already sensitized by contact (by infection) or by immunization with one (or more) strain(s) of influenza virus for which there exists an antigenic relationship with the HA from the virus responsible for the epidemic and in which there exists a certain immunity, even if it is only partially effective, pandemic flu affects a human population not sensitized to a new virus of virus because the HA of this new virus has no or too little an antigenic relationship with the prior circulating viruses.

The epidemic flu vaccine is intended to protect the human population against seasonal flu forms brought about by circulating seasonal influenza viruses that have an antigenic relationship with prior viruses that have already circulated. Currently, the influenza viruses responsible for epidemic flu are of type A and belong to the H1N1 or H3N2 subtypes or are of type B.

The pandemic flu vaccine is intended to protect the human population against infection by a pandemic influenza virus which is a new influenza virus that has no antigenic relationship in terms of the HA with prior circulating viruses. Currently, the influenza virus responsible for pandemic flu is A/H1N1 virus.

The epidemic or pandemic flu vaccine may be in the form of a live attenuated vaccine or an inactivated vaccine, although an inactivated vaccine is preferred for the prevention of pandemic flu. The vaccine may be in the form of a monovalent vaccine (vaccine prepared from a single flu virus strain) or of a multivalent vaccine (vaccine prepared from several flu virus strains). The composition of the epidemic flu vaccine is currently in the form of a trivalent vaccine prepared from the H3N2 and H1N1 viruses and from a type B virus. The inactivated vaccine is generally in the form of whole virus, of fragmented virus (split virus) or of virosomes, or in a subunit form containing HA, and optionally contains one or more adjuvants such as those mentioned above. While the live attenuated vaccine is generally administered orally or nasally to promote the development of mucosal immunity, the inactivated vaccine can be administered parenterally (intramuscularly or subcutaneously), intradermally or even mucosally (intranasally), or even by combining two different routes of administration as described in WO 01/22992. The immunization scheme generally provides for an injection or an injection followed by a booster. The vaccinal dose administered depends on the age of the individual and on the presence or absence of an adjuvant. Conventionally, the vaccinal dose contains the equivalent of 15 μg of HA of each vaccinal strain contained in the vaccine. This dose may be reduced to approximately 1 to 2 μg of HA when the vaccine is adjuvanted, or increased to 30 μg of HA or even more in elderly individuals or individuals suffering from an immune deficiency.

The compositions may be administered using conventional hypodermic syringes or safety syringes such as those commercially available from Becton Dickinson Corporation (Franklin Lakes, N.J., USA) or jet injectors. For intradermal administration, conventional hypodermic syringes may be employed using the Mantoux technique or specialized intradermal delivery devices such as the BD Soluvia(™) micro-injection system (Becton Dickinson Corporation, Franklin Lakes, N.J., USA), may also be employed.

The volume of composition administered will depend on the method of administration. In the case of subcutaneous injections, the volume is generally between 0.1 and 1.0 ml, preferably approximately 0.5 ml.

Throughout this application, various references are cited. The disclosures of these references are hereby incorporated by reference into the present disclosure.

The present invention will be further illustrated by the following figures and examples.

FIGURES

FIG. 1: Illustration of the streamlined scheme for rapid generation of recombinant influenza viruses that could be used as vaccine reassortants. pSP-flu corresponds to the universal vector consisting of the sequence SEQ ID NO: 10.

Figure 2:
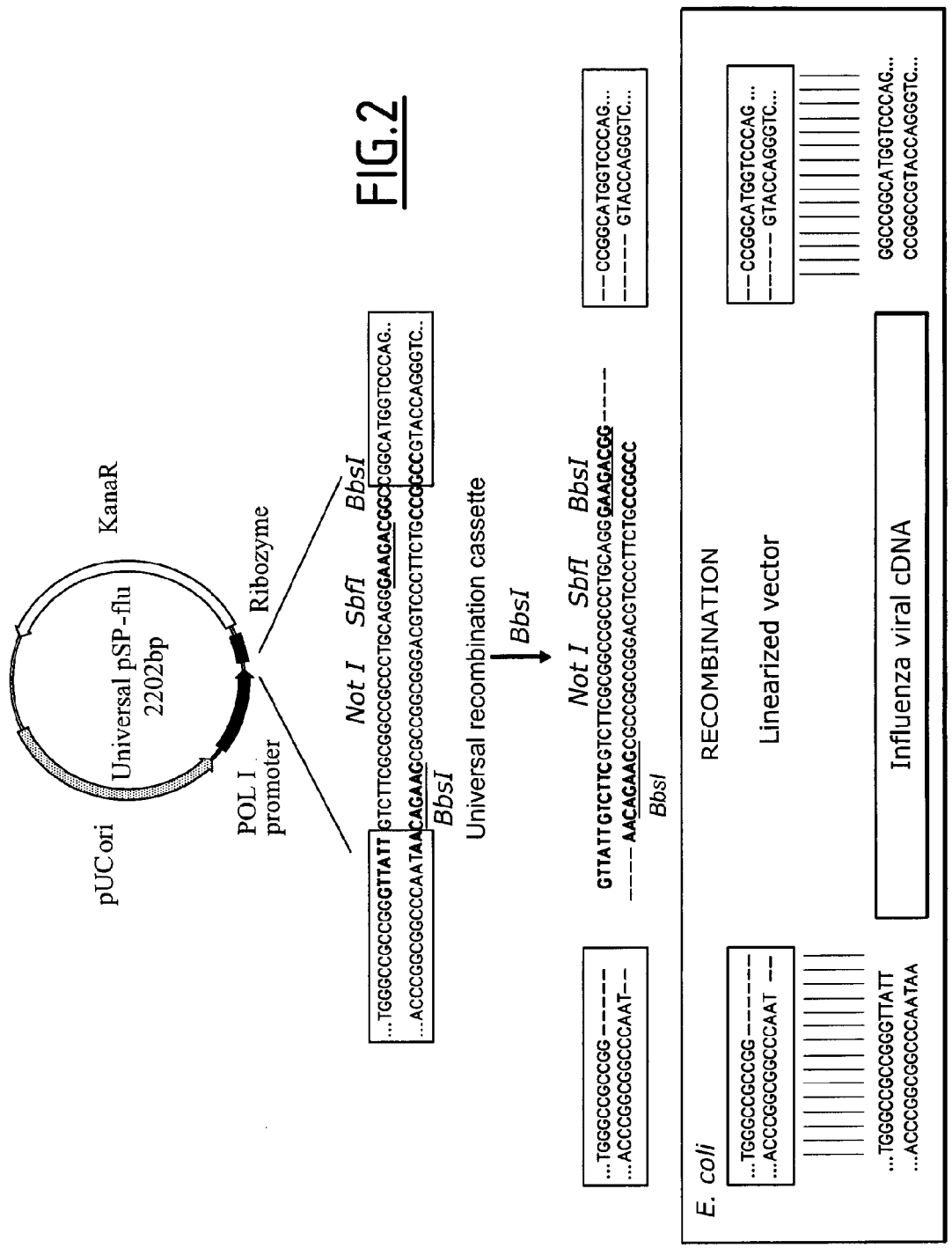

FIG. 2: Cloning strategy using Universal pSP-flu plasmid. The location of kanamycine resistance gene is shown in blank, POL 1 promoter and ribozyme are shown in dark. The plasmid was linearized with Bbsl, and mixed with the viral cDNA containing 17 nucleotides from the promoter and the ribozyme at the ends, before transformation of competent E. Coli. The cDNA recombined into circular plasmid within the regions of terminal complementarity to introduce virus genome segments between POL I promoter and ribozyme. SEQ ID NOs for the sequences in FIG. 2 are as follows: TGGGCCGCCGGGTTATTGTCTTCGCGGCCGCCCT-GCAGGGAAGACGGCCGGC ATGGTCCCAG (SEQ ID NO: 30); ACCCGGCGGCCCAATAACAGAAGCGCCG-GCGGGACGTCCCTTCTGCCGGCCG TACCAGGGTC (SEQ ID NO: 31); TGGGCCGCCGG (SEQ ID NO: 32); ACCCGGCGGCCCAAT (SEQ ID NO: 33); GTTATT-GTCTTCGTCTTCGCGGCCGCCCTGCA-GGGAAGACGG (SEQ ID NO: 34); AACAGAAGCGC-CGGCGGGACGTCCCTTCTGCCGGCC (SEQ ID NO: 35); CCGGCATGGTCCCAG (SEQ ID NO: 36); GTAC-CAGGGTC (SEQ ID NO: 37); TGGGCCGCCGGGTTATT (SEQ ID NO: 38); ACCCGGCGGCCCAATAA (SEQ ID NO: 39); GGCCGGCATGGTCCCAG (SEQ ID NO: 40); CCGGCCGTACCAGGGTC (SEQ ID NO: 41).

EXAMPLE

1. Materials and Methods
1.1. Cells

Suspension of CHOK1 cells (ATCC Number:CCL-61) were cultivated in 125 mL shaker flasks (Thermo Scientific) in Ex-Cell CD CHO fusion medium (SIGMA-ALDRICH, St Quentin Fallavier, FR) supplemented with 4 mM L-glutamine (Gibco®) under agitation. Adherent MDCK cells (CCL-34) and Vero cells (ATCC Number: CCL-81) were cultivated in tissue culture flasks (Becton Dickinson) in DMEM (Gibco®) supplemented with 10% FBS (Thermo Scientific) or in VP-SFM (Gibco®) supplemented with 0.1% povidone K30 (Sanofi Pasteur) respectively. CEP cells were collected from 10-day-old specific pathogen free (SPF) chicken embryos (Valo Biomedia, Osterholz-Scharmbeck, GE) and cultivated in tissue culture flasks (Becton Dickinson) in DMEMF12+Glutamax I (HAM) (Gibco®) supplemented with 5% FBS (Thermo Scientific). All cell cultures were maintained at 37° C. in an atmosphere of 95% air and 5% $CO_2$.

1.2. Receptor Analysis

Analysis of Sia2-3Gal and Sia2-6Gal residue expression on the surface of different cell types was performed using digoxigenin glycan differentiation kit (Roche, Mannhein, Ga.). Two million cells were washed twice in PBS 1× (Eurobio, Courtaboeuf, FR) and once in a buffer containing 0.05 M Tris-HCl, 0.15 M NaCl, 1 mM $MgCl_2$, 1 mM $MnCl_2$ and 1 mM $CaCl_2$, pH 7.5. Cells were incubated for 1 h at room temperature with digoxigenin-labeled lectins *Sambucus nigra* Agglutinin (SNA) (1/1000) specific for Sia2-6Gal residues, or *Maackia amurensis* Agglutinin (MAA) (1/300) specific for Sia2-3Gal. Control cells were incubated without lectins. The cells were washed twice in TBS (0.05 M Tris-HCl, 0.15 M NaCl, pH 7.5) and treated with 1/40 anti-digoxigenin-fluorescein Fab Fragment (Roche) for 1 h at room temperature (in the dark). After two washes in PBS 1× (Eurobio), the cells were analyzed for green fluorescence intensity on Guava capillary cytometer.

1.3. Viruses

Influenza B/Brisbane/60/08 viruses and reassortant vaccine viruses A/New Caledonia/20/99 (H1N1) IVR116, A/Vietnam/1194/04 (H5N1) rg14 and A/California/07/09 (H1N1) X179A were obtained from the NIBSC (Hertfordshire, UK). Viruses were propagated in embryonated hens' eggs (Valo Biomedia) and harvested from infected allantoic fluids.

1.4. Virus Infection

Cells were seeded in 6-well plates (Corning, N.Y., US), 4 h before infection, at a density of $1.6 \times 10^5$ cells/$cm^2$ in the serum-free culture medium appropriate for each cell type, and in a final volume of 1 ml. Infections were performed at various multiplicities of infection (MOI) for 1 h at 35° C. Serum-free culture medium appropriate for each cell type, without serum, (2 ml) containing porcine trypsin (SIGMA-ALDRICH) was added and cells were incubated for 4 days at 35° C. in 8% $CO_2$.

1.5. Hemagglutination Assay

The HA assay was performed by serially diluting 50 μl of culture supernatants 2-fold with PBS 1× (Gibco®) in V-bottom plates (Corning). Subsequently, 50 μl of 0.5% chicken red blood cells (Sanofi Pasteur, Alba-la-Romaine, FR) were added to each well. The plates were incubated for 1 h at 4° C. and the hemagglutination or the absence of hemagglutination was determined visually for each well.

1.6. $TCID_{50}$ Assay

MDCK cells were seeded in 96 well plates (Corning) at a density of $2.7 \times 10^6$ cells/$cm^2$ in DMEM (Gibco®) supplemented with 1 μg/ml porcine trypsin (SIGMA-ALDRICH). Cells were infected with 50 μl of 1:10 serial viral dilutions and incubated for 4 days, at 35° C. Supernatants from these cultures were then tested in a hemagglutination assay. TCID50 titers were calculated according to the statistical method of Spearman-Karber (David John Finney, 1952, Statistical method in biological assay, Hafner editor).

1.7. Transfection Efficiency

Two millions of cells were centrifuged for 10 min at 200×g, resuspended in 100 μl of cGMP (current good manufacturing practices) solution V (Lonza, Basel, CH) at room temperature and 10 μg of pGFP (Sanofi Pasteur) plasmid were added. Nucleoporation was performed with a Nucleofector (Lonza) using different programs. Cells were incubated in 6 well plates (Corning) in the medium optimal for each cell type for 24 h at 37° C., 5% $CO_2$. The cells were analyzed for green fluorescence intensity on Guava capillary cytometer (Millipore, Bellerica, Mass., US).

1.8. Plasmid DNA

The 12 plasmids for the rescue of infectious A/PR/8/34 (H1N1) virus have previously been described by Fodor et al, 1999, J Virol, 73(11):9679-9682. The same methodology was applied with some modifications as mentioned below.

The coding regions of PB2, PB1, PA and NP proteins from A/WSN/33 (H1N1) (WSN) virus were cloned into the pVAX1 plasmid (Life technology, Cergy Pontoise, FR) between the CMV promoter and the bovine growth hormone polyadenylation (BGH-polyA) sites. The pVAX1 plasmid (Life technology) was modified for viral RNA expression. Briefly, a DNA fragment, corresponding to human POL 1 promoter and hepatitis delta ribozyme sequences separated by a linker containing BbsI site for linearization, NotI and SbfI sites, was cloned into the pVAX1 plasmid and the CMV promoter and BGH-polyA site were removed. The resulting plasmid was named "Universal pSP-flu".

Viral RNA was extracted from infected allantoic fluid with QIAamp viral RNA mini kit (Qiagen, Courtaboeuf, FR) and the genomic cDNAs complementary to vRNAs were obtained with a Superscript III one-step RT-PCR system (Life technology) using one pair of primers containing 17 nucleotides from hepatitis delta ribozyme (5'-ctgggaccatgc-cggcc) (SEQ ID NO:11) and 17 nucleotides and from POL 1 promoter (5'-tgggccgccgggttatt) (SEQ ID NO:12) respectively.

The temperature cycle parameters were 47° C. for 60 min, 94° C. for 2 min and then 40 cycles (94° C. for 15 sec, 60° C. for 30 sec and 72° C. for 2 min) and 72° C. for 5 min. Each fragment was subsequently purified with GenElute Gel extraction kit (SIGMA-ALDRICH) and cloned into the Universal pSP-flu plasmid, previously linearized by BbsI (New England Biolabs, Ipswich, Mass., US), by homologous recombination using an In Fusion HD PCR cloning kit (Clontech, Takara Bio, Saint Germain en Laye, FR). Endotoxin free plasmid DNA preparations were generated using a Nucleobond Maxi EF kit (Macherey Nagel, Düren, GE).

1.9. Reverse Genetics

One million Vero and one million CHOK1 cells were mixed and centrifuged for 10 min at 200×g and resuspended in 100 μl of solution V (Lonza) at room temperature. A mixture of 1 μg of each of the 8 vRNA expression plasmids and 0.5 μg of each of the 4 protein expression plasmids was added to the cells and nucleofection was performed with the nucleofector (Lonza) using the U-023 program. Cells were incubated in 6 well plates into Ex-cell™ CD CHO fusion medium (SIGMA-ALDRICH) supplemented with 4 mM L-Glutamine (Gibco®). After 2 h of incubation at 37° C., 5% $CO_2$, 2 million CHOK1 cells were added in the same medium supplemented with recombinant trypsin (TryLE Select) (Gibco®) and incubated on a rotating platform at 35° C., 8% $CO_2$.

1.10. Inhibition Hemagglutination Assay (IHA)

A serum specific for the HA of A/California/07/09 (H1N1) virus, purchased from the National Institute for Biological Standards and Control (NIBSC), was treated with Receptor Destroying Enzyme from Vibrio Cholera (RDE, Sigma, 10 mU/mL) for 18 h at 37° C. The RDE was inactivated at 56° C. for 1 h. The RDE-treated serum was then incubated with 5% turkey Red Blood Cells (RBC) during 2 hours at 4° C. and centrifuged for 10 min at 2000 rpm. Serial dilutions of the treated Serum was then incubated with 4HAU of the virus to be tested for 1 h at room temperature and then with 0.25% chicken RBC for 1 h at 4° C. The IHA titer is determined by the highest dilution of the serum that inhibits the hemagglutination of RBC mediated by the virus.

2. Results 2.1. Cell Growth

MDCK, CHO-K1, Vero, and CEP cells were assessed first for their ability to sustain growth in the most appropriate medium for each cell type either in suspension for CHO-K1 or as adherent for the other cell types. The population doubling level (pdl) was determined for each cell type by estimating the duration necessary for one generation. As seen in Table 1, MDCK and CHO-K1 presented a shorter pdl (23 and 18 h respectively) compared to Vero (38 h), and CEP cells (48 h). It is important to note that CHO-K1 and Vero cell lines were cultivated without serum.

TABLE 1

Population doubling level (pdl) of MDCK, CHO-K1, Vero, and CEP cells.

| Cell type | Population doubling (hours) | S.D. |
|---|---|---|
| MDCK | 23.03 | 3.5 |
| CHO-K1 | 18.0 | 2.6 |
| Vero | 38.4 | 5.1 |
| CEP | 47.66 | 0.5 |

Growth studies were performed over 6 days at 37° C. and population doubling level (pdl) was calculated by estimating the time necessary for one generation. It is calculated from the ratio T/N, wherein T is the duration of the cell culture and N is the number of cell generations calculated from the following equation $Cf=Ci\times 2^N$, wherein Ci and Cf are the initial and final cell concentrations respectively. Values represent the average and standard deviation (S.D.) of three independent experiments.

2.2. Influenza Receptor

During infection, avian viruses as well as the egg-adapted human virus variants mainly bind to Sia2-3Gal linkage, whereas clinical isolates directly isolated from human preferentially bind to Sia2-6Gal linkage (Suzuki et al, 2011, Adv Exp Med Biol, 705:443-452).

To detect the two types of influenza virus receptors on the surface of different cell types, the MAA lectin (specific for Sia2-3Gal linkage) and the SNA lectin (specific for Sia2-6Gal linkage) were used. The cells were incubated for 1 h at room temperature with digoxigenin-labeled lectins *Sambucus nigra* agglutinin (SNA) (specific for Sia2-6Gal) or *Maackia amurensis* agglutinin (MAA) (specific for Sia2-3Gal). Cells were then incubated with anti-digoxigenin-fluorescein Fab fragment and analyzed for fluorescence intensity using the Guava capillary cytometry system. Values displayed in table 2 represent the average and standard deviation (S.D.) of three independent experiments.

MAA and SNA bound strongly to the surface of Vero and MDCK cells (more than 80% of cells) meaning that the two receptors (Sia2-3Gal and Sia2-6Gal) were expressed on MDCK and Vero cells (Table 2). Moreover, MAA bound to 73% of CEP cells whereas SNA only bound to 23% of CEP cells indicating that a high number of CEP cells expressed Sia2-3Gal receptor but a low number expressed Sia2-6Gal. The avian origin of CEP cells could explain why they expressed much more avian receptors than human receptors. CHO-K1 cells do not express Sia2-6Gal receptor, and only weakly Sia2-3Gal receptor.

TABLE 2

Influenza virus receptors on MDCK, CHO-K1, Vero, and CEP cells were analyzed using a digoxigenin glycan differentiation kit.

| Cell type | Type of lectin | Percentages of living cells bound by lectins (%) | S.D. |
|---|---|---|---|
| MDCK | MAA | 93.3 | 3.0 |
| | SNA | 96.4 | 3.8 |
| CHO-K1 | MAA | 31.4 | 3.0 |
| | SNA | 0.0 | 0.0 |
| Vero | MAA | 87.2 | 20.2 |
| | SNA | 83.3 | 11.1 |
| CEP | MAA | 63.3 | 7.4 |
| | SNA | 22.8 | 12.4 |

2.3. Virus Production

Allantoic fluids of influenza viruses were directly put into contact with the cell line to be tested without prior adaptation. Two influenza A reassortants viruses (A/New/Caledonia/20/99 (H1N1) IVR116, and A/Vietnam/1194/04 (H5N1) rg14) and one influenza B virus (B/Brisbane/60/08 lineage B/Victoria/2/87) were tested. Various MOI ($10^{-1}$, $10^{-2}$ and $10^{-3}$) and porcine trypsin concentrations (0, 1, 2, 5 and 8 µg/mL) were used. Results obtained with an MOI of $10^{-1}$ and the most appropriate trypsin concentration after 3 days of infection for type A influenza viruses and after 4 days of infection for type B influenza virus are displayed for each cell type (see Tables 3 and 4).

TABLE 3

Infections of MDCK, CHO-K1, Vero, and CEP cells with influenza A viruses.

| Cell type | Trypsin concentration | A/New Caledonia/20/99 (H1N1) | A/Vietnam/1194/04 (H5N1) |
|---|---|---|---|
| MDCK | 1 µg/ml | 6.4* | 3 |
| CHO-K1 | 2 µg/ml | 7.4 | 3.1 |
| Vero | 2 µg/ml | 6.7 | 2.9 |
| CEP | 2 µg/ml | 4.4 | 3.1 |

*expressed as $\log_{10}$ TCID$_{50}$/ml

TABLE 4

Infections of MDCK, CHO-K1 and Vero cells with influenza B viruses.

| Cell type | Viral titer ($\log_{10}$ TCID$_{50}$/ml) B/Brisbane/60/08 |
|---|---|
| MDCK | 5 |
| CHO-K1 | 4.3 |
| Vero | 4.9 |

A/New Caledonia/20/99 (H1N1) IVR116 and A/Vietnam/1194/04 (H5N1) rg14 reassortants grew on the four cell types tested without the need of prior adaptation. Moreover, the best production of A/New Caledonia/20/99 (H1N1) IVR116 reassortant viruses was observed on CHO-K1 cells that produced the highest viral titers (>$10^7$ TCID50). The production of A/Vietnam/1194/04 (H5N1) rg14 reassortant virus was closely the same on all cell types (approximately $10^3$ TCID50/mL).

With respect to the production of infectious type B viruses, as shown in Table 4, B/Brisbane/60/08 virus replicated well in the three cell lines without the need of prior adaptation.

2.4. Virus Production through the Rescue of Infectious Influenza Viruses by Reverse Genetics Methods 2.4.1. Ability of the Cell Lines to be Transfected It is also important to test the capacity of the different cell types to produce viruses after transfection by a set of expression vectors able to generate infectious influenza viruses. In a first step it is important to test the ability of these different cell types to be transfected, and in particular to be transfected with material that does not involve the use of raw material of animal origin. The nucleoporation technology provided by Amaxa (Amaxa, Lonza technology) that targets the nucleus was used for the transfection of the cells, A green fluorescent protein (GFP) expression plasmid was used to assess the capacity of the different cell lines to be transfected. Cells were resuspended in V solution, incubated with pGFP plasmid and nucleoporated with the nucleofector. Different programs (U-023, A-024, V-001, T-030, L-005) were tested. Cells were then incubated for one day at 37° C. and percentage of green fluorescent cells was analysed by Guava cytometry. The Mean percentage of GFP expressing cells and standard deviation calculated from 3. Independent experiments with the optimal transfection program are displayed in Table 5.

TABLE 5

MDCK, CHO-K1, Vero, and CEP cells susceptibility to nucleoporation.

| Cell type | Nucleoporation program | % of living cells expressing GFP | S.D. |
|---|---|---|---|
| MDCK | A-024 | 71.2 | 26.9 |
| CHO-K1 | U-023 | 74.4 | 15.1 |
| Vero | V-001 | 70.9 | 3.4 |
| CEP | V-001 | 96.4 | 2.3 |

More than 70% of the cells expressed the GFP which means that all the cell lines tested are transfectable by nucleoporation.

2.4.2. Optimization of the Influenza cDNA Cloning Step

To be efficient, the flu vaccine, which usually contains the antigenic material derived from two type A viruses and one type B virus, must be updated every year depending on the new circulating viruses that appear and are responsible for seasonal flu or pandemic flu. Importantly, the HA and NA antigenic material must be updated so that it corresponds to that of the new circulating virus. To perform reverse genetics the HA and NA encoding genes must be cloned in the vRNA expression plasmid under the control of a POL I promoter every year or when a new circulating virus has been characterized. The other vRNA plasmids encoding the internal A/PR/8/34 vRNA and the protein expression plasmids are usually constructed only once. As the cloning step in the vRNA expression plasmid could be very tricky when reverse genetics is done on unknown HA and NA genes, a universal reverse genetics plasmid that could be used for the cloning by recombination of any influenza segments from type A and B viruses was developed. But the strict requirement for precise initiation and termination of the vRNA transcripts dramatically limits the choice of recombination regions. Thus, a new recombination cassette, not specific for the influenza genome, comprising the last 17 nucleotides of the POL 1 promoter and the first 17 nucleotides of the hepatitis delta ribozyme was used. Furthermore, 28 nucleotides, comprising BbsI to linearize the circular plasmid, NotI and SbfI sites to exclude empty plasmid were incorporated between the POL 1 promoter and the hepatitis delta ribozyme. The resulting plasmid, named "Universal pSP-flu" is relatively small (2202pb) and contained a kanamycin resistance gene (FIG. 2). To prepare influenza cDNA for cloning, vRNAs were reverse transcribed into cDNAs containing the recombination ends, and were cloned between the POL 1 promoter and the ribozyme. Using this improved RNA production plasmid, several genes from influenza A and B viruses were cloned by homologous recombination. The proportion of positive clones was greater than 90% for "easy" cloning and 30% for "tough" cloning with an average of 150 clones per cloning experiment.

The universal pSP-flu plasmid so developed presents several improvements for easy and rapid influenza genome cloning. The recombinant cassette can be used to clone every influenza RNA fragments from type A and B virus. Secondly, as it is difficult to be sure that linearized vectors were free of empty plasmids that generate background colonies, Universal pSP-flu plasmid contains three enzymatic sites (BbsI, SbfI and NotI) that can be used to remove any residual empty plasmids after the cloning step. Linearization with BbsI enzyme, containing a cleavage point outside of the recognition site, generated cohesive ends and enabled the recircularization of plasmid.

2.4.3. Rescue of Influenza Viruses

The CHO-K1 and Vero cell lines based on their good growth properties were tested for their ability to rescue infectious influenza virus by reverse genetics.

Porcine trypsin generally used to rescue influenza virus by reverse genetics was replaced by a highly purified and animal origin-free enzyme (TrypLE™ Select) from Gibco. In a first experiment, the rescue of reassortant viruses containing HA and NA vRNA from A/WSN/33 (H1N1) virus and the six remaining viral genes (PB1, PB2, PA, NP, M and NS) from A/PR/8/34 (H1N1) virus was performed by nucleoporation of the twelve plasmids (4 plasmids allowing the expression of PB1, PB2, NA and NP mRNA under the control of human POL II promoter and 8 plasmids allowing the expression of the 8 vRNAs under the control of human POL I promoter) into Vero and/or CHO-K1. No viral particles were obtained after transfection of Vero or CHO-K1 cells alone but, when Vero cells were mixed with CHO-K1 cells, viruses were detected by hemagglutination assay in the supernatants of the cell mixture as soon as 2 days after transfection.

Furthermore it was easy to visualize signs of an infection in the mixture of nucleoporated Vero/CHO-K1. Indeed, after a four days culture, the cells transfected without plasmids were clearly individualized whereas the cells transfected with the twelve plasmids and shedding viral particles in the supernatant were aggregated. Various influenza virus reassortant viruses were rescued very rapidly using this technique containing the internal backbone (PB1, PB2, PA, NP, M and NS) of the A/PR/8/34 (H1N1) virus and expressing the HA and NA proteins from different influenza viruses such as A/WSN/33 (H1N1), A/PR/8/34 (H1N1), A/NC/20/99 (H1N1) IVR116, A/Solomon Island/03/06 (H1N1) IVR145, A/Vietnam/1194/04 (H5N1) rg14, A/Brisbane/10/07 IVR-147 (H3N2), A/Uruguay/716/07 (H3N2) X175C, and AN/Wisconsin/67/05 (H3N2) X161b.

Results obtained were highly reproducible from one experiment to another and most of the time optimal titers were obtained five days after transfection. For example, a reassortant virus containing the HA and NA from A/Vietnam/1194/04 (H5N1) rg14 was produced in the cell culture supernatant with a titer as high as 128 HAU/50 µl after transfection of a mixture of Vero/CHOK1 using three different nucleoporation programs (U-023, U-027, F-014). Other reassortant viruses containing the HA and NA from the A/H1N1 or A/H3N2 viruses cited above reached similar titers (up to 256-512 HAU/50 µl) five days after transfection. The corresponding TCID50 titers varied between 4 and 7 log10 TCID50/ml.

An improved reverse genetics system is described in this study using two cell lines, namely Vero and CHO-K1 that are suitable to be used for human vaccine production. As shown by the viral infection study, several A/H1N1 and A/H5N1 viruses or reassortant viruses were easily recovered using the mixture of Vero/CHO-K1 cells. In the same way A/H3N2 viruses were also rescued demonstrating that this system can be used for the production of reassortant of any pandemic and seasonal viruses. Viruses can be recovered directly from the Vero/CHO-K1 supernatant and titrated by HAU assay as soon as two days after transfection. When the virus shall be produced at an industrial scale, for instance in the frame of a human or veterinary vaccine production, the supernatant can be used as a seed to further infect a stock of CHO-K1 cells Furthermore as it was shown in the examples, the generation of infectious influenza viruses by reverse genetics using a mixture of Vero and CHO-K1, or the production of virus by direct infection of CHO-K1 cells with an infectious viral seed does not require the use of serum and/or biological material of animal origin. The infectious influenza viruses such produced are therefore more secure since the possible contamination by adventitious agents like viruses, mycoplasma and prions no longer exists. Furthermore the lack of serum in the media used during tranfection and/or infection steps facilitates the purification process and makes easier the flu vaccine manufacturing. To our knowledge it is the first time that a totally animal free process to rescue influenza virus by reverse genetics is described.

3. Production of Chimeric Influenza Viruses by Reverse Genetics 3.1. Construction of HA and NA Chimeric Genes The chimeric constructs were assembled first in silico using the software Vector NTI. The HA chimeric gene A/California/07/09-A/PR/8/34 (H1N1) contains the non-coding regions (NCR), the signal peptide (SP), the HA2 domain, the transmembrane (TM) domain and the Cyto domain of the the A/PR/8/34 (H1N1) virus and the HA1 domain from the A/California/07/09 (H1N1) virus.

The NA chimeric gene A/California/07/09-A/PR/8/34 (H1N1) contains the non-coding regions (NCR), the transmembrane (TM) domain, the Cyto domain and the stalk of the A/PR/8/34 (H1N1) virus, and the ectodomain from the A/California/07/09 (H1N1) virus.

Once these sequences have been determined, the corresponding HA and HA chimeric genes were synthesized and cloned in the Universal pSP-flu plasmid.

3.2. Production of the Chimeric Influenza Virus by Reverse Genetics

Production of the chimeric influenza viruses by reverse genetics was performed as described hereabove, i.e. by using four plasmids for expression of the viral proteins PB1, PB2, PA and NA, and eight plasmids for expression of the vRNAs PB1, PB2, PA, NP, NS, M, chimeric HA and chimeric NA which were introduced into the mixture of CHO-K1/Vero cells by nucleoporation as mentioned earlier. The produced viruses are "bi-chimeric" since they contain two chimeric genes. They contain the PB2, PA, NP, NS, and M genes from the A/PR/8/34 (H1N1) virus, the PB1 gene from the A/California/07/09 (H1N1) virus, the HA chimeric gene A/California/07/09-A/PR/8/34 (H1N1) and the NA chimeric gene A/California/07/09-A/PR/8/34 (H1N1). The A/NC/20/99 (H1N1) virus was used as positive control for each reverse genetics experiment.

In a first experiment the trypsin concentration to be used was determined. Among the trypsin concentrations tested (1 to 6 USP/ml), only the trypsin concentrations of 3 and 4 USP/ml allow the production of chimeric influenza viruses (Table 6). In the subsequent experiments it was shown that a, concentration of 4 USP/ml is slightly better than 3 USP/ml since the hemagglutinin titer was slightly higher (64 HAU/50 μl compared to 32 HAU/50 μl).

TABLE 6

Determination of the trypsin concentration necessary to obtain the chimeric A/California/07/09-A/PR/8/34 (H1N1) influenza virus by reverse genetics.

| | | | HAU/50 μl Day(s) after | | |
|---|---|---|---|---|---|
| | Reverse genetics experiments | Trypsin | nucleoporation | | |
| N° | Viruses potentially produced | (USP/ml) | D + 5 | D + 6 | D + 7 |
| 1 | A/NC/20/99 (H1N1) reassortant | 2 | 128 | 128 | 64 |
| 2 | chimeric A/California/07/09- | 1 | <1 | <1 | <1 |
| 3 | A/PR/8/34 (H1N1) | 2 | <1 | <1 | <1 |
| 4 | | 3 | 2 | 16 | 32 |
| 5 | | 4 | 4 | 32 | 64 |
| 6 | | 5 | <1 | <1 | <1 |
| 7 | | 6 | <1 | <1 | <1 |

The production of chimeric reassortant A/California/07/09-A/PR/8/34 (H1N1) was reproducible. The chimeric virus was detectable in the cell culture supernatant from the fifth day post-nucleoporation and optimally produced at the eighth or ninth day post-nucleoporation.

"Mono-chimeric" viruses containing either a chimeric HA gene or a chimeric NA gene were also successfully produced by reverse genetics using the chimeric HA A/California/07/09-A/PR/8/34 (H1N1) gene and the NA gene from the A/PR/8/34 (H1N1) virus or the chimeric NA A/California/07/09-A/PR/8/34 (H1N1) gene and the HA gene from the A/PR/8/34 (H1N1) virus.

3.3. Assessment of the HA Protein Antigenicity Produced by the Chimeric Virus

To verify that the use of a HA chimeric gene did not alter the antigenicity of the HA protein expressed by the chimeric virus, we compared the titers obtained in the inhibtion hemagglutination assay as described in 1.10 using as tested virus either the reassortant A/California/07/09 (H1N1) virus or the "bi-chimeric" virus as obtained in 3.2. The higher the titers in the inhibition hemagglutination assay, the stronger was the recognition of the HA antigen by the antibody. The IHA titers obtained with the two virus tested were higher than 10240 which means that the antigenicity of the HA protein expressed by the bi-chimeric virus is well conserved and very similar or identical to that of A/California/07/09 (H1N1) reassortant.

4. Comparison of the Production of Reassortant Influenza Virus in Two Mixtures of Cells: Vero/CEF and Vero/CHO-K1 Cells One million Vero cells were resuspended in solution V (Lonza) at room temperature. A mixture of 1 μg of each of the 6 vRNA expression plasmids expressing the vRNA of PB1, PB2, PA, NP, M and NS of the A/PR/8/34 (H1N1) virus, 1 μg of each of the 2 vRNA expression plasmids expressing the vRNA of NA and HA of the A/Vietnam/1203/04 (H5N1) virus, and 0.5 μg of each of the 4 protein expression plasmids expressing the mRNA of PB1, PB2, PA, NP of the A/PR/8/34 (H1N1) virus was added to the cells and nucleofection was performed with the nucleofector (Lonza) using the V-001 program. Cells were incubated in 6 well plates into 1.5 ml of DMEM-F12® medium (Gibco®). After 2 h of incubation at 37° C., 5% $CO_2$, one million CEF (Chicken embryo fibroblasts) cells were added in the same medium supplemented with porcine trypsin (Sigma) and incubated on a rotating platform at 35° C., 8% $CO_2$ At regular intervals, 100 μl of supernatant culture were collected in order to evaluate the viral titer with a hemagglutination assay. The results of the hemagglutination assay are presented in the Table 7 below.

Five hundred thousand Vero and five hundred thousand CHO-K1 cells were mixed and were resuspended in solution V (Lonza) at room temperature. A mixture of 1 μg of each of the 6 vRNA expression plasmids expressing the vRNA of PB1, PB2, PA, NP, M and NS of the A/PR/8/34 (H1N1) virus, 1 μg of each of the 2 vRNA expression plasmids expressing the vRNA of NA and HA of the A/Vietnam/1203/04 (H5N1) virus, and 0.5 μg of each of the 4 protein expression plasmids expressing the mRNA of PB1, PB2, PA, NP of the A/PR/8/34 (H1N1) virus was added to the cells and nucleofection was performed with the nucleofector (Lonza) using the U-023 program. Cells were incubated in 6 well plates into Ex-cell™ CD CHO fusion medium (SIGMA-ALDRICH) supplemented with 4 mM L-Glutamine (Gibco®). After 3 h of incubation at 37° C., 5% $CO_2$, one million CHOK1 cells were added in the same medium supplemented with porcine trypsin (Sigma) and incubated on a rotating platform at 35° C., 8% $CO_2$ (the final concentration of trypsin being then at 2 μg/ml). At regular intervals, 100 μl of supernatant culture were collected in order to evaluate the viral titer with a hemagglutination assay. The results of the hemagglutination assay are presented in the Table 7 below.

TABLE 7

Viral titer of the culture supernatant (UHA/50 μl).

| | D4 | D5 | D6 | D7 | D12 |
|---|---|---|---|---|---|
| Vero/CEF | <1 | <1 | 4 | 32 | 128 |
| Vero/CHO | 32 | 512 | 64 | NT | NT |

D: Day after transfection.
NT: Not tested.

The results show that Vero/CHO-K1 cell system allows the production of reassortant influenza virus only four days after transfection whereas it necessitates at least 7 days for producing the same amount of reassortant influenza virus using the Vero/CEF system. The Vero/CHO-K1 cell system also allows producing a high amount of reassortant virus (512 UHA/50 μl). Thus the results demontrates that the Vero/CHO-K1 cell system is more efficient than the Vero/CEF cell system for producing reassortant influenza virus.

The invention claimed is:

1. A method for producing infectious influenza viruses, wherein said method comprises the steps of:
   a) transfecting a mixture of cells comprising CHO cells and cells of primate origin, wherein the cells of primate origin comprise Vero cells, 293T cells, or PER.C6 cells, with a set of expression vectors to generate a seed of infectious influenza virus, and
   b) infecting CHO cells with said seed of infectious influenza virus.

2. The method according to claim 1, wherein the cells of step b) are CHO-K1 cells that do not express Sia2-6Gal receptors.

3. The method according to claim 1, wherein the cells of primate origin are Vero cells.

4. The method according to claim 1, wherein said set of expression vectors comprises:
   (a) expression vectors allowing the expression of one or more mRNAs encoding at least influenza PB1, PB2, PA, NP, M, NS, HA, and NA proteins, and
   (b) expression vectors allowing the expression of one or more influenza PB1, PB2, PA, NP, M, NS, HA and NA vRNAs, or the corresponding cRNAs,
wherein the expression of said set of expression vectors allows (i) the formation of the ribonucleoprotein complex (RNP) containing the influenza vRNA(s), and (ii) the generation of infectious influenza viruses in the transfected cells.

5. The method according to claim 4, wherein:
   (i) said expression vectors allowing the expression of one or more mRNAs encoding influenza PB1, PB2, PA, NP, M, NS, HA, and NA proteins comprise four different uni directional plasmids, each plasmid containing one or more cDNAs complementary to a mRNA encoding one of the four distinct proteins selected from PB1, PB2, PA and NP influenza proteins, wherein the one or more cDNAs are under the control of a promoter that binds to RNA polymerase II, and
   (ii) said expression vectors allowing the expression of influenza PB1, PB2, PA, NP, M, NS, HA and NA vRNAs, or the corresponding cRNAs, comprise eight different uni directional plasmids, each plasmid containing one or more cDNAs complementary to one of the eight distinct vRNAs selected from said PB1, PB2, PA, NP, M, NS, HA and NA influenza vRNAs, or to the corresponding cRNAs, wherein the one or more cDNAs are under the control of a promoter that binds to RNA polymerase I.

6. A method for producing infectious influenza viruses, wherein said method comprises the steps of:
   a) transfecting cells with a set of expression vectors to generate a seed of infectious influenza virus, and
   b) infecting CHO cells with said seed of infectious influenza virus, wherein said set of expression vectors comprises:
   (aa) expression vectors allowing the expression of one or more mRNAs encoding at least influenza PB1, PB2, PA, NP, M, NS, HA, and NA proteins, and
   (bb) expression vectors allowing the expression of one or more influenza PB1, PB2, PA, NP, M, NS, HA and NA vRNAs, or the corresponding cRNAs,
   wherein the expression of said set of expression vectors allows the formation of the ribonucleoprotein complex (RNP) containing the influenza vRNA(s), and the generation of infectious influenza viruses in the transfected cells, and
   (i) said expression vectors allowing the expression of one or more mRNAs encoding influenza PB1, PB2, PA, NP, M, NS, HA, and NA proteins comprise four different uni directional plasmids, each plasmid containing one or more cDNAs complementary to a mRNA encoding one of the four distinct proteins selected from PB1, PB2, PA and NP influenza proteins, wherein the one or more cDNAs are under the control of a promoter that binds to RNA polymerase II, and
   (ii) said expression vectors allowing the expression of influenza PB1, PB2, PA, NP, M, NS, HA and NA vRNAs, or the corresponding cRNAs, comprise eight different uni directional plasmids, each plasmid containing one or more cDNAs complementary to one of the eight distinct vRNAs selected from said PB1, PB2, PA, NP, M, NS, HA and NA influenza vRNAs, or to the corresponding cRNAs, wherein the one or more cDNAs are under the control of a promoter that binds to RNA polymerase I;
   wherein each plasmid in paragraph (ii) has been obtained by cloning said cDNA into a vector comprising, in the 5' to 3' sense:
   a) a promoter that binds to RNA polymerase I, or a T7 RNA polymerase;

b) a recombination cassette comprising, in the 5' to 3' sense:
an inverted complementary recognition sequence for a first restriction enzyme which has its cutting site outside of its recognition sequence and produces sticky ends;
a restriction site for a second restriction enzyme which has its cutting site inside of its recognition sequence;
a restriction site for a third restriction enzyme which has its cutting site inside of its recognition sequence; and
a recognition sequence for said first restriction enzyme which has its cutting site outside of its recognition sequence and produces sticky ends;
wherein said second and third restriction enzymes are different; and
c) a terminator sequence; wherein:
when the promoter binds to RNA polymerase I, said terminator sequence is hepatitis delta ribozyme sequence; and
when the promoter binds to T7 RNA polymerase, said terminator sequence is T7 polymerase terminator sequence.

7. The method according to claim 6, wherein said vector comprises sequence SEQ ID NO: 1.

8. The method of claim 4, wherein said set of expression vectors comprises eight different bidirectional plasmids, each plasmid containing a cDNA complementary to one of the eight distinct vRNAs selected from said PB1, PB2, PA, NP, M, NS, HA and NA influenza vRNAs under the control of two promoters, wherein said first promoter binds to polymerase I and said second promoter binds to polymerase II.

9. The method of claim 1, wherein the infectious influenza viruses produced are reassortant infectious type A or type B influenza viruses, wherein the genetic material comprises a combination of the genetic material of at least two donor viruses, wherein one of the donor viruses is A/Puerto Rico/8/34 (H1N1) (A/PR/8/34), B/Lee/40 or B/Panama/45/90.

10. The method according to claim 1, wherein the infectious influenza viruses produced are chimeric viruses that contain a chimeric influenza HA and/or NA vRNAs, wherein the chimeric influenza HA vRNA and/or NA vRNAs comprise one or more domains of a HA vRNA or one or more domains of a NA vRNA from a clinical isolate of influenza virus and one or more domains of a HA vRNA or one or more domains of a NA vRNA from another donor virus, wherein at least one domain of the HA vRNA from said clinical isolate of influenza virus is complementary to the region of a mRNA encoding the antigenic ectodomain of HA, and at least one domain of the NA vRNA from said clinical isolate of influenza virus is complementary to the region of a mRNA encoding the antigenic ectodomain of NA from said clinical isolate of influenza virus.

11. The method according to claim 1, wherein said method is entirely performed in a serum-free medium or in animal component-free conditions.

12. A method of preparing an influenza vaccine composition, which method comprises:
a) producing influenza viruses by a method according to claim 1;
b) harvesting the infectious influenza viruses after multiplication in CHO cells,
c) purifying the harvested infectious influenza virus,
d) optionally inactivating the purified virus, and
e) mixing the purified virus with a pharmaceutically acceptable carrier.

13. A method of preparing an influenza vaccine composition, which method comprises:
a) producing influenza viruses by transfecting cells with a set of expression vectors to generate a seed of infectious influenza virus, and infecting CHO cells with said seed of infectious influenza virus;
b) harvesting the infectious influenza viruses after multiplication in CHO cells,
c) purifying the harvested infectious influenza virus,
d) optionally inactivating the purified virus, and
e) mixing the purified virus with a pharmaceutically acceptable carrier, wherein at least one of the expression vectors comprises, in the 5' to 3' sense:
a promoter that binds to RNA polymerase I, or to T7 RNA polymerase;
a recombination cassette comprising, in the 5' to 3' sense:
an inverted complementary recognition sequence for a first restriction enzyme which has its cutting site outside of its recognition sequence and produces sticky ends;
a restriction site for a second restriction enzyme which has its cutting site inside of its recognition sequence;
a restriction site for a third restriction enzyme which has its cutting site inside of its recognition sequence; and
a recognition sequence for said first restriction enzyme which has its cutting site outside of its recognition sequence and produces sticky ends;
wherein said second and third restriction enzymes are different; and
a terminator sequence;
wherein:
when the promoter binds to RNA polymerase I, said terminator sequence is hepatitis delta ribozyme sequence,
when the promoter binds to T7 RNA polymerase, said terminator sequence is T7 polymerase terminator sequence.

14. The method of claim 3, wherein the CHO cells of step a) are CHO-K1 cells, and a mixture of Vero cells and CHO-K1 cells is transfected.

15. The method of claim 1, wherein the CHO cells of step a) are CHO-K1 cells.

* * * * *

SEQUENCE LISTING

<160> NUMBER OF SEQ ID NOS: 41

<210> SEQ ID NO 1
<211> LENGTH: 363
<212> TYPE: DNA
<213> ORGANISM: Artificial Sequence
<220> FEATURE:
<223> OTHER INFORMATION: Vector

<400> SEQUENCE: 1
cgggccggcc cctgcgtgtg gcacgggcgg ccgggagggc gtccccggcc cggcgctgct      60
cccgcgtgtg tcctggggtt gaccagaggg ccccggcgc tccgtgtgtg gctgcgatgg     120
tggcgttttt ggggacaggt gtccgtgtcg cgcgtcgcct gggccggcgg cgtggtcggt     180
gacgcgacct cccggccccg ggggaggtat atctttcgct ccgagtcggc attttgggcc    240
gccgggttat tgtcttcgcg gccgccctgc agggaagacg gccggcatgg tcccagcctc    300
ctcgctggcg ccggctgggc aacattccga ggggaccgtc cctcggtaa tggcgaatgg     360 gac                                                                  363

<210> SEQ ID NO 2
<211> LENGTH: 28
<212> TYPE: DNA
<213> ORGANISM: Artificial Sequence
<220> FEATURE:
<223> OTHER INFORMATION: Recombination cassette

<400> SEQUENCE: 2
gtcttcgcgg ccgccctgca gggaagac                                        28

<210> SEQ ID NO 3
<211> LENGTH: 84
<212> TYPE: DNA
<213> ORGANISM: Artificial Sequence
<220> FEATURE:
<223> OTHER INFORMATION: hepatitis delta ribozyme terminator sequence

<400> SEQUENCE: 3
ggccggcatg gtcccagcct cctcgctggc gccggctggg caacattccg aggggaccgt     60
cccctcggta atggcgaatg ggac                                            84

<210> SEQ ID NO 4
<211> LENGTH: 47
<212> TYPE: DNA
<213> ORGANISM: Artificial Sequence
<220> FEATURE:
<223> OTHER INFORMATION: T7 polymerase terminator sequence

<400> SEQUENCE: 4
ctagcataac cccttggggc ctctaaacgg gtcttgaggg gttttttt                  47

<210> SEQ ID NO 5
<211> LENGTH: 223
<212> TYPE: DNA
<213> ORGANISM: Artificial Sequence
<220> FEATURE:
<223> OTHER INFORMATION: Rodent RNA pol1 promoter

<400> SEQUENCE: 5
ctcttggtcc tatcacggtt atgaggtcga ccagttgttg ctttgatgtt cggttctctc      60
gttgattggg acaatatttg gggcacttcg ccggtcccga cttccagaat tccgtgtgg     120

```
tctgtgaatt tatcaccgct acactgtcat catattccag ttttgcaatc tgctctcttt     180
gtacctgcag ataggtactg acacgcttgt cttgtgagtg ggt                       223
```

<210> SEQ ID NO 6
<211> LENGTH: 770
<212> TYPE: DNA
<213> ORGANISM: Artificial Sequence
<220> FEATURE:
<223> OTHER INFORMATION: Rodent RNA pol1 promoter

<400> SEQUENCE: 6

```
gtcgaccaga agccttttaa aagtccttca cgtcccgtaa ctgtaactaa ccctcggtcc      60
ccggcggtgg tctcggcgac ccgaggccga gaggaagcgc tgttcccgga ttcactagcg    120
ggccgggacc cgggattctc tgggtgcctc ggaacatttt atcttgtgtg cgtgcggtag    180 ccacccrtcgg tcgatccccg gcggtggtct cggcgacccg aggccgagag gaagcgctgt    240
tcccggattc actagcgggc cggggcccgg gattctctgg gtgcctcgga acttttcctt    300
ctgcggaagc cctcggtccc cagcggtcgt ctcggcgtct cgaagccgag aggaggcgct    360
gtttccggcc tcactgcctg ctagttcccg gttccttgta gggtcagact tttgttttc    420 ttcgacgtgt cctcccatcc cgggctcctg cctccgggtc cttgcccgag aggatgccgg    480
tgtgtgccga tcttttctgc atgtctacct cgctcttggt cctatcacgg ttatgaggtc    540
gaccagttgt tgctttgatg ttcggttctc tcgttgattg ggacaatatt tggggcactt    600
cgccggtccc gacttccaga atttccgtgt ggtctgtgaa tttatcaccg ctacactgtc    660
atcatattcc agttttgcaa tctgctctct ttgtacctgc ataggtac tgacacgctt       720 gtcttgtgag tgggtgacat tagtaaagga ctgctctcgg gcttttctg               770
```

<210> SEQ ID NO 7
<211> LENGTH: 268
<212> TYPE: DNA
<213> ORGANISM: Artificial Sequence
<220> FEATURE:
<223> OTHER INFORMATION: Rodent RNA pol1 promoter

<400> SEQUENCE: 7

```
gtcgaccagt tgttcctttg aggtccggtt cttttcgtta tggggtcatt tttgggccac      60
ctccccaggt atgacttcca ggtattctct gtggcctgtc actttcctcc ctgtctcttt    120
tatgcttgtg atcttttcta tctgttccta ttggacctgg agataggtac tgacacgctg    180
tcctttccct attaacacta aaggacacta taaagagacc ctttcgattt aaggctgttt    240
tgcttgtcca gcctattctt tttactgg                                         268
```

<210> SEQ ID NO 8
<211> LENGTH: 251
<212> TYPE: DNA
<213> ORGANISM: Artificial Sequence
<220> FEATURE:
<223> OTHER INFORMATION: Human RNA pol1 promoter

<400> SEQUENCE: 8

```
cgggccggcc cctgcgtgtg gcacgggcgg ccgggagggc gtccccggcc cggcgctgct      60
cccgcgtgtg tcctggggtt gaccagaggg ccccgggcgc tccgtgtgtg gctgcgatgg    120
tggcgttttt ggggacaggt gtccgtgtcg cgcgtcgcct gggccggcgg cgtggtcggt    180
gacgcgacct cccggccccg ggggaggtat atctttcgct ccgagtcggc attttgggcc    240
gccgggttat t                                                          251
```

<210> SEQ ID NO 9
<211> LENGTH: 29
<212> TYPE: DNA
<213> ORGANISM: Artificial Sequence
<220> FEATURE:
<223> OTHER INFORMATION: T7 RNA polymerase promoter

<400> SEQUENCE: 9
tattgtaata cgactcacta tagggtctt                              29

<210> SEQ ID NO 10
<211> LENGTH: 2202
<212> TYPE: DNA
<213> ORGANISM: Artificial Sequence
<220> FEATURE:
<223> OTHER INFORMATION: Universal pSP-flu plasmid

<400> SEQUENCE: 10
gactcttcgc gatgtacggg ccagatatac gcgtcgggcc ggccctgcg tgtggcacgg      60 gcggccggga gggcgtcccc ggccggcgc tgctcccgcg tgtgtcctgg ggttgaccag     120
agggccccgg gcgctccgtg tgtggctgcg atggtggcgt ttttggggac aggtgtccgt    180
gtcgcgcgtc gcctgggccg gcggcgtggt cggtgacgcg acctcccggc ccgggggag    240 gtatatcttt cgctccgagt cggcattttg gccgccggg ttattgtctt cgcggccgcc    300
ctgcagggaa gacggccggc atggtcccag cctcctcgct ggcgccggct gggcaacatt   360 ccgagggac cgtcccctcg gtaatggcga atggactga tcaagagaca ggatgaggat    420
cgtttcgcat gattgaacaa gatggattgc acgcaggttc ccggccgct tgggtggaga    480 ggctattcgg ctatgactgg gcacaacaga caatcggctg ctctgatgcc gccgtgttcc    540
ggctgtcagc gcaggggcgc ccggttcttt ttgtcaagac cgacctgtcc ggtgccctga    600
atgaactgca agacgaggca gcgcggctat cgtggctggc cacgacgggc gttccttgcg    660
cagctgtgct cgacgttgtc actgaagcgg gaagggactg gctgctattg ggcgaagtgc    720
cggggcagga tctcctgtca tctcaccttg ctcctgccga gaaagtatcc atcatggctg    780
atgcaatgcg gcggctgcat acgcttgatc cggctacctg cccattcgac caccaagcga    840
aacatcgcat cgagcgagca cgtactcgga tggaagccgg tcttgtcgat caggatgatc    900
tggacgaaga gcatcagggg ctcgcgccag ccgaactgtt cgccaggctc aaggcgagca    960
tgcccgacgg cgaggatctc gtcgtgaccc atggcgatgc ctgcttgccg aatatcatgg   1020
tggaaaatgg ccgcttttct ggattcatcg actgtggccg ctgggtgtg gcggaccgct   1080 atcaggacat agcgttggct acccgtgata ttgctgaaga gcttggcggc gaatgggctg   1140
accgcttcct cgtgctttac ggtatcgccg ctcccgattc gcagcgcatc gccttctatc   1200
gccttcttga cgagttcttc tgaattatta acgcttacaa tttcctgatg cggtatttc    1260 tccttacgca tctgtgcggt atttcacacc gcatacaggt ggcactttc ggggaaatgt    1320 gcgcggaacc cctatttgtt tattttctta aatacattca aatatgtatc cgctcatgag    1380
acaataaccc tgataaatgc ttcaataata gcacgtgcta aaacttcatt tttaatttaa    1440
aaggatctag gtgaagatcc ttttgataa tctcatgacc aaaatccctt aacgtgagtt    1500
ttcgttccac tgagcgtcag accccgtaga aaagatcaaa ggatcttctt gagatccttt    1560 tttctgcgc gtaatctgct gcttgcaaac aaaaaaacca ccgctaccag cggtggtttg    1620
tttgccggat caagagctac caactctttt tccgaaggta actggcttca gcagagcgca    1680
gataccaaat actgtccttc tagtgtagcc gtagttaggc caccacttca agaactctgt    1740

```
agcaccgcct acatacctcg ctctgctaat cctgttacca gtggctgctg ccagtggcga    1800
taagtcgtgt cttaccgggt tggactcaag acgatagtta ccggataagg cgcagcggtc    1860
gggctgaacg gggggttcgt gcacacagcc cagcttggag cgaacgacct acaccgaact    1920
gagataccta cagcgtgagc tatgagaaag cgccacgctt cccgaaggga gaaaggcgga    1980
caggtatccg gtaagcggca gggtcggaac aggagagcgc acgagggagc ttccagggggg   2040 aaacgcctgg tatctttata gtcctgtcgg gtttcgccac ctctgacttg agcgtcgatt    2100
tttgtgatgc tcgtcagggg gcggagcct atggaaaaac gccagcaacg cggccttttt     2160
acggttcctg gcttttgct ggccttttgc tcacatgttc tt                        2202
```

```
<210> SEQ ID NO 11
<211> LENGTH: 17
<212> TYPE: DNA
<213> ORGANISM: Artificial Sequence
<220> FEATURE:
<223> OTHER INFORMATION: Reverse primer

<400> SEQUENCE: 11
ctgggaccat gccggcc                                                    17

<210> SEQ ID NO 12
<211> LENGTH: 17
<212> TYPE: DNA
<213> ORGANISM: Artificial Sequence
<220> FEATURE:
<223> OTHER INFORMATION: Forward primer

<400> SEQUENCE: 12
tgggccgccg ggttatt                                                    17

<210> SEQ ID NO 13
<211> LENGTH: 2233
<212> TYPE: DNA
<213> ORGANISM: Influenza A virus

<400> SEQUENCE: 13
agtagaaaca aggtactttt ttggacagta tggatagcaa atagtagcac tgccacaact      60
aactcaatgc atgtgtaagg aaggagttga accaagaagc attaagcaaa acccagggat     120
cattaatcag gcactcctca attgcttcat atagccccc aagatcaaag gtcccaggtt      180
ctaggttgtc cctaagagcc tgaacgataa gaagcagttt tcttgattca gctgaaaatc     240
cttctagttg tggagatgca tacaagctgt tgaataccga cttttgctaat aaagtcctgc    300 agaccttccc aatggaactt tcctccactc cttttgggga ctctccaatg ggccatgttt     360
ctgatttgtt ctcaaagaac tcttttggtca tgtcttctc tttgacagag gactcagctt     420
caatcatact ctcaatttgt tgaagtgact ggaggaggca acgcctcatc tccattcccc     480
atttcatttt aattttttgag gttccatttg ttctcacata caagaacatg gccttgaaa    540 cctggcctat ggcacttctt ataagcatat ctcctatctc aagaacacag tacttctccc      600
atttatgtgg ttcaagtctt gggtcagtga gagaaaactc catgctcaca agtttaccca     660
cgtcggtgtc attccttaag tgggatcttc ctttatgat gaaaccatac aagttggtct      720
ttcgccttcc ctccttagtt ctacacttgc ttatcattgg aattaattgg aaatcatcca     780
ttgctgcaca agatgcatta agcaaggcag tattgatgta caccccctc attatgtatt      840 ctgtggctct gcagtgagac acctctgatg tgaaataatt ccttctcatg cttgcaatgt     900
gttcaattgg agccacatct tctccaatct catcgagctc tatccagctt gaatctgtca    960
```

-continued

```
gttcgcatgc cttgttaaac tcattctgaa tccaacttgc aagcgacctc aattctggtt    1020
catcactatc atattgcttc aaatcaccta catctttaca gtcgtcaaag tctacctttt    1080
ctggtgccat gttctcacca agtgcccact ttagctgact tgttttcttc atattttttag   1140
tctttggaat tttctcctca ttctcaatgt cctgcagttc tgccagtact tgcttccatg    1200
acagaagata atttggattt attccctttt cgtgtggttt aacaacattg ggttccttcc    1260
atccaaagaa tgttctcatg catttgattg catcatatag cggtattccc tctccttcat    1320
gacttgggtc ctcaatgctt aattttaagg catccatcag caggaatttg gaccgctgag    1380
aacagggagg cccattcgga agtctaagtg gtcgtggtgt tgttttcaaa aaaggttcaa    1440
ttctagcatt tacttctttg acatttgag acagcttgcc ctcaatgtag ccgttcggtt     1500
cgaatccatc cacataggct ctaaaatttt caaggctgga aagttcggc gggagacttt     1560
ggtcggcaag cttgcgcatt gttcctgtga tttcaaacct ttcttcaatt gtctcttctc    1620
ctctctcgga ctgacgaaag gaatcccaga ggcctctgct ggccatttct tgtcttatgg    1680
tgaatagtct ggttttgatc ctagccctgc tttcttcatc gagagtgtag tctgcctttg    1740
tggccatttc ttccccagtg aacgagaaaa tgtggatgtg tgttttctca gatttaattt    1800
tattggcctt ttcagatag tatatgtgaa cttctctcct tgttactcca atttcgatga     1860
atctattctc cttgtaatca tacaaatctg gtagaaactt tggtttctca gcccctgtag    1920
tgttgcaaat actgtttact actgtccagg ccattgtgcg atctcttccc tcgattattt    1980
caaatctgtg cttcaaaagt gcatttggat caccaagttc tacgattatt gactcgcctt    2040
gctcattgat gaagtgaaaa tctgaataca tgaagcatac ttccaagtga gtgcatattg    2100
ctgcaaattt gtttgtttcg attttcaggt cctccccata ctctttcatt gttttttccg    2160
caagctcgac aatcatcgga ttgaagcatt gtcgcacaaa atcttccatt ttggatcagt    2220
acctgctttc gct                                                      2233
```

<210> SEQ ID NO 14
<211> LENGTH: 2341
<212> TYPE: DNA
<213> ORGANISM: Influenza A virus

<400> SEQUENCE: 14

```
agtagaaaca aggcattttt tcatgaagga caagctaaat tcactatttt tgccgtctga      60
gctcttcaat ggtggaacag atcttcatga tctcagtgaa ctcttctttc tttatccttc     120
cagattcgaa atcaatccgt gcatcaattc gggctctgga aaccatagcc tccaccatac     180
tggatatccc gactggtctt ctgtatgaac tgctggggaa gaattttttca aataaattgc    240
agcacctttg gtacatttgt tcatcctcaa gtactcctct ttgacttgta ttcaagatgg     300
atcgatttct tttggggatc caggagtgtg ttgttgcaac agcatcatac tccatgtttt     360
tggctggacc atgtgctggc atcatcactg cattgttcat tgattcaatt tctttatggc    420
tgacaaatgg gttcagtggg ttgcataaac gcccctggta atcctcatcc atcaattccc    480
attttaggca gacttcagga atgtggagat ttctaatgtt gtataaattt gggcctccgt    540
cggagaccag cagtccagct ttggaacggg tttgctccca cagtttcttt atttcaaatg    600
atcttcgggt ttgtatttgt gtgtcacctc tatggcatcg gtacgtgtac ctgtaatctt    660
tgatgaacaa ctgaagggcc atttgagctg ttgctggacc aagatcattg tttatcatat    720
tgttttgat gacagtaact ccaatactca gtccgctga ctcgttgatc ccagacaccc       780
caaaactggg aagctccatg ctgaaattgg caacaaaccc ataacgatag aaaaaacttg    840
```

-continued

```
tgaattcaaa tgtacctgtt ctgtttatgt aagacttttt cttgctcata ttgattccaa    900
gtagcttaca ggttcgataa aacctgtcga ctccggcttg aatcccttca tgattgggtg    960
cattcacaat cagagcaaaa tcgtcagagg attgaagacc atcccaccag taagtagtct   1020
tggtgtatct cttttgtcca agattcagga tggagacgcc taatacagtg cttaacatat   1080
tgaacatgcc catcatcatt ccagggctca atgatgcagt cccctctatt aagagcggtc   1140
ggattttttc aatcttcttt cttgttgaat cattgaaata tttcaaatcg atgcttgcta   1200
gcatttctgc aggtatttga gttctaagtt tcatactctt gctctcaaac atataccctt   1260
ttcccagtct cgccattttg tttgagaaca ttattggagc aatacttaga acatttctga   1320
accattcggg ctgatttctg gtcatatatg tgatcatggc caaaaacatc cgaggattct   1380
gattttcgtt ccatttggtg ttatctccag tgatggtgaa agaaagttcg gtgtcctgag   1440
aattggtcat catcttcctt acaacatttg ccaactttgc tttcttctca ttgcctccaa   1500
ctggcaaccc tgattgttca agtttctcac atatactcct tgccagtgtc tcaacaaagt   1560
atacaaaccc ccttatttgc atccctgggg ttgcaattgc tctccgtttt agcttccctc   1620
tctcagcatc tttggtcatt gtgttcaggg tcaatgctct aattagataa ctccttttgt   1680
tcaatctctg cttcttttta cccattgttc tctgtgttat cattttctta gtcatattgt   1740
ctctcacccg tctctttctc tgaaaatgag ttgtgatccc catttcttct ttgttcattg   1800
actccattac atccttaagg aagtctatga gccttccaga ctcattggcc gtgaggccat   1860
ttgatctgaa cacttctatt gtgttggcca atgctgttgc agcaggttgg tttctattta   1920
gagtccagtc ataggtctgt cggccttgtg tcagcttgtc tactcgtgtt tgctgaacaa   1980
cctccatcgt ttcaatacac gagttttcaa aaataccagg atgggattcc tcaaggaaag   2040
ccatcgcctc caatacacaa tctgtttggg cataaccact tggttcattg tcttctggca   2100
gtggcccatc aatcgggttg agttgcggtg ctccagtttc ggtgtttgtt gtccatcttc   2160
ccttttctga gtactgatgt gtcctgttga cagtatccat ggtgtatcct gttcctgtcc   2220
catggctgta aggagggtct ccagtataag ggaaagttgt gcttatagca ttttgtgctg   2280
gcacttttaa gaaaagtaag gtcggattga catccattca aatggtttgc ctgctttcgc   2340
t                                                                   2341
```

<210> SEQ ID NO 15
<211> LENGTH: 2341
<212> TYPE: DNA
<213> ORGANISM: Influenza A virus

<400> SEQUENCE: 15

```
agtagaaaca aggtcgtttt taaactattc gacactaatt gatggccatc cgaattcttt     60
tggtcgctgt ctggctgtca gtaagtatgc tagagtcccg tttccgtttc attaccaaca    120
ccacgtctcc ttgcccaatt agcacattag ccttctctcc tttcgcaagg ttgctcagtt    180
cattgatgct tagtgctggc ccatatctct tgtcttcttt gcccagaatg aggaatcccc    240
tcagaacagc ggactccact ccagctgtgc cttcatctgg gtcttcagtt aaagtgccag    300
catcctttcc gagaactgtg agtctcttcg tggccttgtt atagttgaat acaggagaat    360
tgccccttac aagtattctc attcctgatc ccctcacatt cacagtaaat gaggagaact    420
gcattctact ttgctttggt ggagcggctg cgaagggaag aagttttatt atctgtgcgg    480
tatcaaatgt cccaagcaca tccctcattt gttggaacag agttcttaca aacccactgt    540
attggcctct aatggcctta ggtactaaag actgaaatgg ttcaaattcc attttattgt    600
```

-continued

```
atagcattgt agggttctgg gaccactgaa ttttaacagt ttcccagttt ctgatgatcc    660
attgataggt attgaccaac actgattcag gaccattaat ctcccacatc attgacgatg    720
agtaagttat tgtcagtttc tctgttccct gtgtttcact gacctcctcg ggagacagta    780
gtacatttcc tcgttggtcc cggattctca aaaaacggtc aatgctcacc actaccctct    840
ccgtgctgga gtactcatct acacccattt tgctgattct cactcctctc attgacatct    900
cgatgcttgg agtcatgtcg ggcaatatcc caatcattcc catcacattg tcgataggtt    960
caactcccca attttgaaaa agcactttcg catccttctg aaaatgtctt aaaagttgat   1020
gcataggatt caatcgctga ttcgccctat tgacgaaatt cagatcacct ctgactgctt   1080
ttatcataca atcctcttgt gaaaatacca tggccacaat tattgcttcg gcaatcgact   1140
gttcgtctct cccactcact atcagctgaa tcaatctcct ggttgctttt ctgagtatgg   1200
ctgttgctct tctcccaacc attgtgaact cttcatatcc ctcatgcact cttatcttca   1260
atgtttgaag attgcccgta agcacctctt cctctctctt gactgatgat ccgcttgttc   1320
tcttaaatgt gaatccacca aaactgaagg atgagctaat tctcagtccc attgcagcct   1380
tgcatatatc cacggcttgc tcttctgttg ggttctgcct aaggatgtct accatcctaa   1440
ttccaccaat ctgtgtgctg tggcacatct ccaataaaga tgctagtgga tctgctgata   1500
ctgcagctct tctcactatg ttcctagcag caataatcaa gctttggtca acatcatcat   1560
tcctcacttc ccctcctgga gtatacatct gttcccagca tgttccttga gtcaaatgca   1620
acacttcaat gtacacactg cttgttccac cagccactgg gaggaatctc gttttgcgga   1680
ccagttctct ctccaacatg tatgcaacca tcaaaggaga aattttgcaa tcctggagtt   1740
cttctttctt ctctttggtt atcgttagtt gcgattccga tgttagtatc ctggctccca   1800
cttcgttagg gaaaacaact tccatgatta catcctgtgc ctccttggca ctgagatctg   1860
catgaccagg atttatgtca actctccgac gtattttgac ttggtttcta aaatggacag   1920
ggccaaaggt tccatgcttt agcctttcga ctctttcaaa ataagttttg tagatttttg   1980
gataatgaac tgtatttgtt attggtccat tcctattcca ccatgtcaca gccagaggtg   2040
ataccatcac tcggtctgat ccggcatcat tcattttact ccataaagtt tgtccttgct   2100
catttctctc aggaatcatt tccgttatcc tcttgtctgc tgtaattgga tatttcattg   2160
ccatcatcca tttcatccta agtgctgggt tcttctcctg tcttcctgat gtgtacttct   2220
tgattatggc catatggtcc acggtggttt ttgtgagtat ctcgcgggtg cgagactgcg   2280
acattagatt tcttagttct tttattcttt ccatattgaa tataattgac ctgctttcgc   2340
t                                                                   2341
```

```
<210> SEQ ID NO 16
<211> LENGTH: 1565
<212> TYPE: DNA
<213> ORGANISM: Influenza A virus

<400> SEQUENCE: 16
agtagaaaca agggtatttt tctttaattg tcgtactcct ctgcattgtc tccgaagaaa     60
taagatcctt cattactcat gtcaaaggaa ggcacgatcg ggctcgctgc cttttcgtcc    120
gagagctcga agactccccg cccctggaaa gacacatctt ctggtcttgc actttccatc    180
atccttatga tttcggtcct catgtcagat gttctcccct ctgtattccc attgaatgct    240
gccataatgg ttgttctgtc aaaagggaga tttctctgta ctgagaacgt aggttgtatg    300
ctgatttggc ccgcagatgc cctctgttga ttggtgtttc ctccacttct ggtccttatg    360
```

```
gcccagtacc tgcttctcag ttcaagtgta cttgattcca tagtctccat attttcattg    420
gaagcaattt gaactcctct agtggaaagc ttccctcttg ggagcacctt cgtccctttg    480
atgaagctta atactcttag atcttcaaat gcggcagaat ggcatgccat ccacaccagt    540
tgactcttgt gtgctggatt ctcatttggt ctgattaggc tgtacacttg gctgttttga    600
agcagtctga aagggtctat tccgactaga gagtatccct ctctttcaaa gtcgtaccca    660
ctggctacgg caggtccata cacacaggca ggcaggcagg acttgtgagc aaccgaccct    720
ctcaatatga gtgcagaccg tgctagaaaa gtgagatctt cgaactcagc attccctggg    780
ttccggctct ctctcacttg atccatcatt gcttttgtg cagcagtttg aaatttccct     840 tgagaatgt tgcacattct ttcataagca attcttgttt ttcgtccatt ctcacccctc     900
cagaagttcc gatcattgat cccacgtttg atcatcctga ccaattccat caccattgtt    960
ccaactcctt tgactgcagc acctgcggct ccagacctcc tagggagagt tgaaccttgc    1020
atcagagagc acatcctggg atccattccg gtgcgaacaa gagctcttgt cctctgataa    1080
gttgcatcat tcaaattgga atgccagatc atcatgtgag tcagaccagc cgttgcatcg    1140
tcaccattat tagcttggcg ccagattcgc cttatttctt ctttgtcata aggatgagt    1200 tctctcatcc actttccgtt tactctcctg tatataggtc ctccagtttt cttaggatct    1260
ttccccgcac tgggatgttc ttccaggtat ttatttctcc tttcgtcaaa gcagagagc    1320 accattctct ctattgttaa gctgttttgg atcaaccgtc cctcataatc actgagtttg    1380
agttcggtgc acatttggat gtagaatcgt ccaattccac caatcatttt tccgacggat    1440
gctctgattt cagtggcatt ctggcgttct ccatcagtct ccatctgttc gtaagaccgt    1500
ttggtgcctt gggacgccat gattttgatg tcactcagtg agtgattatc taccctgctt    1560
ttgct                                                                1565

<210> SEQ ID NO 17
<211> LENGTH: 1027
<212> TYPE: DNA
<213> ORGANISM: Influenza A virus

<400> SEQUENCE: 17
agtagaaaca aggtagtttt ttactccagc tctatgctgg caaaatgacc atcgtcagca     60
tccacagcac tctgctgttc ctttcgatat tcttccctca tagactttgg cacccctcc    120 gtagaaggcc ctcctttcag tccgtattta aagcgacggt aaatgcattt gaaaaaaaga    180
cgatcaagaa tccacaatgt caagtgcaag atcccaatga tatttgcggc aatagtgaga    240
ggatcacttg aaccgttgca tctgcacccc cattcgtttc tgataggcct gcaaattttc    300
aagaagatca tttttcagac cagcactgga gctaggatga gtcccaatgg ttctcatcgc    360
ttgcaccatt tgtctagcct gactagcaac ctccatggcc tctgctgctt gctcactcga    420
tccagccatt tgctccatag ccttagctgt agtgctggca aaaccattc tgttctcatc     480 tctgattagt ggattggttg ttgtcaccat tgcctatga ccgatgct gggagtcagc      540 aatctgttca caggttgcac ataccaggcc aaatgccact cagtggtca gccccccat     600 cctgttgtat atgaggccca tacaactggc aagtgcacca gcagaataac tgagtgagat    660 ttcttggcc ccatggaatg ttatctccct cttgagcttc ctatacagtt taactgcttt     720
gtccatgtta tttggatccc cgttcccatt aagggcattt tggacaaagc gtctacgctg    780
cagtcctcgc tcactgggca cggtgagcgt gaacacaaat cctaaaatcc ccttagtcag    840
aggtgacagg attggtcttg tctttagcca ttccatgaga acctcaagat cggtgttctt    900
```

| | | |
|---|---|---|
| ccctgcaaag acatcttcaa gtctctgtgc gatctcggct ttgagggggc ctgacgggat | 960 | |
| gatagagagt acgtacgttt cgacctcggt tagaagactc atctttcaat atctacctgc | 1020 | |
| tttcgct | 1027 | |

<210> SEQ ID NO 18
<211> LENGTH: 890
<212> TYPE: DNA
<213> ORGANISM: Influenza A virus

<400> SEQUENCE: 18

| | |
|---|---|
| agtagaaaca agggtgtttt ttattactaa ataagctgaa acgagaaagt tcttatctct | 60 |
| tgctccactt caagcaatag atgtaaggct tgcataaatg ttatttgctc aaaactattc | 120 |
| tctgttatct tcagtttgtg tctcacttct tcaatcaacc atcttatttc ttcaaacttc | 180 |
| tgacctaatt gttcccgcca tttctcgttt ctgttttgga gtgagtggag gtctcccatt | 240 |
| ctcattactg cttctccaag cgaatctctg tagagtttca gagactcgaa ctgtgttatc | 300 |
| attccattca agtcctccga tgaggactcc aactgcattt ttgacatcct cagcagtatg | 360 |
| tcctggaaga gaaggcaatg gtgaaatttc gccaacaatt gctccctctt cggtgaaagc | 420 |
| ccttagcaat attagagtct ccagccggtc aaaaatcaca ctgaagttcg ctttcagtat | 480 |
| gatgttctta tccatgatcg cctggtccat tctgatacaa agagggcctg ccactttctg | 540 |
| cttgggtatg agcatggacc agtcccttga catttcctca agagtcatgt cagttaggta | 600 |
| acgcgacgca ggtacagagg ccatggtcat tttaagtgcc tcatcggatt cttctttcag | 660 |
| aatccgctcc actatctgct ttccagcacg tgtggctgtc tcgatgtcca gaccgagagt | 720 |
| gctgcccctt cctcttaggg atttctgatc tcggcgaagc cgatcaagga atggggcatc | 780 |
| acctagttct tggtctgcaa ctcgtttgcg gacatgccaa agaaagcaat ctacctgaaa | 840 |
| gcttgacaca gtgtttggat ccattatgtt tttgtcaccc tgcttttgct | 890 |

<210> SEQ ID NO 19
<211> LENGTH: 45
<212> TYPE: DNA
<213> ORGANISM: Artificial Sequence
<220> FEATURE:
<223> OTHER INFORMATION: NCR domain of HA

<400> SEQUENCE: 19

| | |
|---|---|
| agtagaaaca agggtgtttt tcctcatatc tctgaaattc taatc | 45 |

<210> SEQ ID NO 20
<211> LENGTH: 32
<212> TYPE: DNA
<213> ORGANISM: Artificial Sequence
<220> FEATURE:
<223> OTHER INFORMATION: NCR domain of HA

<400> SEQUENCE: 20

| | |
|---|---|
| tttggttgtt tttattttcc cctgcttttg ct | 32 |

<210> SEQ ID NO 21
<211> LENGTH: 51
<212> TYPE: DNA
<213> ORGANISM: Artificial Sequence
<220> FEATURE:
<223> OTHER INFORMATION: SP domain of HA

<400> SEQUENCE: 21

| | |
|---|---|
| tgcatctgca gctgcaagtg cacataacag gaccagtagg tttgccttca t | 51 |

```
<210> SEQ ID NO 22
<211> LENGTH: 255
<212> TYPE: DNA
<213> ORGANISM: Artificial Sequence
<220> FEATURE:
<223> OTHER INFORMATION: HA2 domain of HA

<400> SEQUENCE: 22
ctgatagatc cccattgatt ccaatttcac tccatctacc ttttccctgt tcaactttga      60
ctcttctgaa tatttgggat aatcataagt cccatttctt acactttcca tgcattcatt     120
gtcacacttg tggtagaact caaaacatcc atttccgatt tctttggcat tattctttaa     180
ttggcttttt actttctcat acagattctt cacatttgag tcatggaaat ccagagtcct     240 ttcatttttcc agtag                                                    255

<210> SEQ ID NO 23
<211> LENGTH: 75
<212> TYPE: DNA
<213> ORGANISM: Artificial Sequence
<220> FEATURE:
<223> OTHER INFORMATION: TM domain of HA

<400> SEQUENCE: 23
catccagaaa ctgattgccc ccagggagac caaaagcacc agtgaactgg cgacagttga      60
gtagatcgcc agaat                                                      75

<210> SEQ ID NO 24
<211> LENGTH: 39
<212> TYPE: DNA
<213> ORGANISM: Artificial Sequence
<220> FEATURE:
<223> OTHER INFORMATION: Cyto domain of HA

<400> SEQUENCE: 24
tcagatgcat attctgcact gcaaagatcc attagaaca                            39

<210> SEQ ID NO 25
<211> LENGTH: 28
<212> TYPE: DNA
<213> ORGANISM: Artificial Sequence
<220> FEATURE:
<223> OTHER INFORMATION: NCR domain of NA

<400> SEQUENCE: 25
agtagaaaca aggagttttt tgaacaga                                        28

<210> SEQ ID NO 26
<211> LENGTH: 20
<212> TYPE: DNA
<213> ORGANISM: Artificial Sequence
<220> FEATURE:
<223> OTHER INFORMATION: NCR domain of NA

<400> SEQUENCE: 26
tttaaactcc tgctttcgct                                                 20

<210> SEQ ID NO 27
<211> LENGTH: 93
<212> TYPE: DNA
<213> ORGANISM: Artificial Sequence
<220> FEATURE:
<223> OTHER INFORMATION: TM domain of NA
```

<400> SEQUENCE: 27
tgaatggcta atccatattg agattatatt ccctatttgc aatattaggc taattagtcc    60
gactaccaga cagattgatc caatggttat tat                                 93

<210> SEQ ID NO 28
<211> LENGTH: 105
<212> TYPE: DNA
<213> ORGANISM: Artificial Sequence
<220> FEATURE:
<223> OTHER INFORMATION: Stalk domain of NA

<400> SEQUENCE: 28
gccggttaat atcactgaag ttgtgtcctt tacccaggtg ctattttat aggtaatgat     60 gttttggttg catattccag tatggttttg acttccagtt tgaat                   105

<210> SEQ ID NO 29
<211> LENGTH: 18
<212> TYPE: DNA
<213> ORGANISM: Artificial Sequence
<220> FEATURE:
<223> OTHER INFORMATION: Cyto domain of NA

<400> SEQUENCE: 29
tttctgattt ggattcat                                                  18

<210> SEQ ID NO 30
<211> LENGTH: 62
<212> TYPE: DNA
<213> ORGANISM: Artificial Sequence
<220> FEATURE:
<223> OTHER INFORMATION: Universal pSP-flu plasmid fragment

<400> SEQUENCE: 30
tgggccgccg ggttattgtc ttcgcggccg ccctgcaggg aagacggccg gcatggtccc    60
ag                                                                   62

<210> SEQ ID NO 31
<211> LENGTH: 62
<212> TYPE: DNA
<213> ORGANISM: Artificial Sequence
<220> FEATURE:
<223> OTHER INFORMATION: Universal pSP-flu plasmid fragment

<400> SEQUENCE: 31
ctgggaccat gccggccgtc ttccctgcag ggcggccgcg aagacaataa cccggcggcc    60
ca                                                                   62

<210> SEQ ID NO 32
<211> LENGTH: 11
<212> TYPE: DNA
<213> ORGANISM: Artificial Sequence
<220> FEATURE:
<223> OTHER INFORMATION: POL I promoter fragment

<400> SEQUENCE: 32
tgggccgccg g                                                         11

<210> SEQ ID NO 33
<211> LENGTH: 15
<212> TYPE: DNA
<213> ORGANISM: Artificial Sequence
<220> FEATURE:
<223> OTHER INFORMATION: POL I promoter fragment

```
<400> SEQUENCE: 33
taacccggcg gccca                                                     15

<210> SEQ ID NO 34
<211> LENGTH: 42
<212> TYPE: DNA
<213> ORGANISM: Artificial Sequence
<220> FEATURE:
<223> OTHER INFORMATION: Universal recombination cassette

<400> SEQUENCE: 34
gttattgtct tcgtcttcgc ggccgccctg cagggaagac gg                        42

<210> SEQ ID NO 35
<211> LENGTH: 36
<212> TYPE: DNA
<213> ORGANISM: Artificial Sequence
<220> FEATURE:
<223> OTHER INFORMATION: Universal recombination cassette

<400> SEQUENCE: 35
ccggccgtct tccctgcagg gcggccgcga agacaa                               36

<210> SEQ ID NO 36
<211> LENGTH: 15
<212> TYPE: DNA
<213> ORGANISM: Artificial Sequence
<220> FEATURE:
<223> OTHER INFORMATION: Ribozyme promoter fragment

<400> SEQUENCE: 36
ccggcatggt cccag                                                     15

<210> SEQ ID NO 37
<211> LENGTH: 11
<212> TYPE: DNA
<213> ORGANISM: Artificial Sequence
<220> FEATURE:
<223> OTHER INFORMATION: Ribozyme promoter fragment

<400> SEQUENCE: 37
ctgggaccat g                                                         11

<210> SEQ ID NO 38
<211> LENGTH: 17
<212> TYPE: DNA
<213> ORGANISM: Artificial Sequence
<220> FEATURE:
<223> OTHER INFORMATION: Influenza viral cDNA fragment

<400> SEQUENCE: 38
tgggccgccg ggttatt                                                   17

<210> SEQ ID NO 39
<211> LENGTH: 17
<212> TYPE: DNA
<213> ORGANISM: Artificial Sequence
<220> FEATURE:
<223> OTHER INFORMATION: Influenza viral cDNA fragment

<400> SEQUENCE: 39
aataacccgg cggccca                                                   17
```

```
<210> SEQ ID NO 40
<211> LENGTH: 17
<212> TYPE: DNA
<213> ORGANISM: Artificial Sequence
<220> FEATURE:
<223> OTHER INFORMATION: Influenza viral cDNA fragment

<400> SEQUENCE: 40
ggccggcatg gtcccag                                                    17

<210> SEQ ID NO 41
<211> LENGTH: 17
<212> TYPE: DNA
<213> ORGANISM: Artificial Sequence
<220> FEATURE:
<223> OTHER INFORMATION: Influenza viral cDNA fragment

<400> SEQUENCE: 41
ctgggaccat gccggcc                                                    17
```